(12) United States Patent
Ryu et al.

(10) Patent No.: US 8,168,177 B2
(45) Date of Patent: May 1, 2012

(54) METHOD OF REGULATING MAMMALIAN TARGET-OF-RAPAMYCIN ACTIVITY BY INTERACTION BETWEEN PHOSPHOLIPASE D AND RHEB

(75) Inventors: Sung-Ho Ryu, Pohang (KR); Pann-Ghill Suh, Pohang (KR); Sang-Hoon Ha, Pohang (KR); Mi-Nam Lee, Pohang (KR); Hyun-Ju Lee, Pohang (KR); Il-Shin Kim, Pohang (KR); Do-Hyung Kim, Minneapolis, MN (US); Tae-Hoon Lee, Pohang (KR)

(73) Assignee: Postech Academy-Industry Foundation, Pohang (KR)

( * ) Notice: Subject to any disclaimer, the term of this patent is extended or adjusted under 35 U.S.C. 154(b) by 566 days.

(21) Appl. No.: 12/374,239

(22) PCT Filed: Aug. 3, 2007

(86) PCT No.: PCT/KR2007/003754
§ 371 (c)(1),
(2), (4) Date: Jan. 16, 2009

(87) PCT Pub. No.: WO2008/016282
PCT Pub. Date: Feb. 7, 2008

(65) Prior Publication Data
US 2009/0304667 A1 Dec. 10, 2009

Related U.S. Application Data

(60) Provisional application No. 60/821,542, filed on Aug. 4, 2006.

(51) Int. Cl.
*A61K 38/46* (2006.01)
*C12N 9/14* (2006.01)
(52) U.S. Cl. ...................................... 424/94.6; 435/195
(58) Field of Classification Search .................... None
See application file for complete search history.

(56) References Cited

FOREIGN PATENT DOCUMENTS
WO WO-2004/026898 4/2004

OTHER PUBLICATIONS

International Search Report and Written Opinion for PCT/KR2007/003754 dated Nov. 13, 2007.
Ha et al., "PLD2 forms a functional complex with mTOR/raptor to transduce mitogenic signals," *Cellular Signalling*, 18:2283-2291 (2006).
Hay et al., "Upstream and downstream of mTOR," *Genes Dev.*, 18:1926-1945 (2004).
Hornberger et al., "The role of phospholipase D and phosphatidic acid in the mechanical activation of mTOR signaling in skeletal muscle," *PNAS*, 103:4741-4746 (2006).
Long et al., "Rheb binding to mammalian target of rapamycin (mTOR) is regulated by amino acid sufficiency," *J. Bio. Chem*, 280:23433-23436 (2005).

*Primary Examiner* — Nashaat Nashed
(74) *Attorney, Agent, or Firm* — Marshall, Gerstein & Borun LLP

(57) ABSTRACT

The present invention relates to method of regulating mammalian target-of-rapamycin (mTOR) based on a novel finding of a regulating mechanism of mTOR by a phospholipase D (PLD), and Ras homolog enriched in brain (Rheb). Further, the present invention also relates to a method of screening inhibitors of mTOR, and a method and a composition for treating mTOR-related metabolic diseases by inhibiting mTOR.

3 Claims, 12 Drawing Sheets

<Inactive>

<Transition>

<Active>

METHOD OF REGULATING MAMMALIAN TARGET-OF-RAPAMYCIN ACTIVITY BY INTERACTION BETWEEN PHOSPHOLIPASE D AND RHEB

CROSS REFERENCE TO RELATED APPLICATION

This application claims priority to and the benefit of Provisional Application No. 60/821,542 filed on Aug. 4, 2006, which is hereby incorporated by reference for all purposes as if fully set forth herein.

BACKGROUND OF THE INVENTION (a) Field of the Invention

The present invention relates to method of regulating mammalian target-of-rapamycin (mTOR) based on a novel finding of a mechanism of regulating mTOR by a phospholipase D (PLD), and a Ras homolog enriched in brain (Rheb). Further, the present invention also relates to a method of screening inhibitors of mTOR, and a method and a composition for treating mTOR-related metabolic diseases by inhibiting mTOR.

(b) Description of the Related Art mTOR is a serine/threonine protein kinase and a member of a novel superfamily of signaling proteins termed PI 3-kinase related kinases (PIKKs), based on sequence similarity of their catalytic domains. The mTOR pathway is an emerging target for the treatment of cancer, diabetes, obesity, hamartoma syndromes, tissue/organ hypertrophy, etc. Recent studies have demonstrated its role as a mediator of lifespan control in *C. elegans* and *Drosophila*. Despite the significance of this pathway in such diverse biological processes, the mechanism of its regulation by nutrients remains unknown.

In addition, mTOR requires the lipid second messenger phosphatidic acid (PA) for its activation. PA is an enzymatic product of PLD. PLD, which hydrolyzes phosphatidylcholine (PC) to generate PA, constitutes another branch of the mTOR upstream regulators through which mitogenic signals impinge on the mTOR pathway. Mammalian PLD isozymes identified to date, PLD1 and PLD2, sense a variety of signals, such as neurotransmitters, hormones and growth factors, to regulate multiple physiological events such as proliferation, secretion, respiratory burst and actin cytoskeletal reorganization, and the like.

PA binds to mTOR and activates its activity to phosphorylate S6K1 and 4EBP1, two known downstream effectors of mTOR19. However, the mechanism by which PA activates mTOR in cells remains unknown. Recently, the inventors found that PLD2 specifically forms a functional complex with the mTOR/raptor complex to transducer mitogenic signals, and suggested that the localized generation of PA is essential for PLD2 activation of mTOR kinase activity as provided by the interaction with raptor through TOS motif in PLD2 (Ha, S. H., Kim, D. H., Kim, I. S., Kim, J. H., Lee, M. N., Lee, H. J., Kim, J. H., Jang, S. K., Suh, P. G., Ryu, S. H. PLD2 forms a functional complex with mTOR/raptor to transduce mitogenic signals. *Cell. Signal.* 18 (2006) 2283-2291, which is hereby incorporated by reference). The above identification of PLD2 as a functional and physical mediator for the mTOR/raptor complex led the inventors to test the interrelations between PLD2 and Rheb, to complete the present invention.

SUMMARY OF THE INVENTION

An aspect of the present invention is to reveal a mechanism of regulating mTOR activity by PLD and Rheb. More specifically, the mTOR activity may be activated by the steps of 1) binding of Rheb to mTOR through PLD2 by interaction between PLD2 and Rheb;

2) movement of PA produced from PLD2 near mTOR, to increase the level of PA near mTOR; and 3) binding of Rheb to mTOR due to the increase of PA near mTOR, to activate the mTOR kinase activity.

Based on the above, another aspect of the present invention is to provide a method of regulating mTOR activity by regulating one or more steps among the following steps:

1) binding of Rheb to mTOR through PLD2 by interaction between PLD2 and Rheb;

2) movement of PA produced from PLD2 near mTOR, to increase the level of PA near mTOR; and 3) binding of Rheb to mTOR due to the increase of PA near mTOR, to activate the mTOR kinase activity.

Another aspect of the present invention is to provide a method of screening inhibitors of mTOR activity. The method of screening inhibitors of mTOR according to the present invention may comprising the steps of:

contacting a candidate compound to a sample cell;

examining the interaction between PLD2 and Rheb by which Rheb is capable of binding to mTOR through PLD2; and determining the compound as an inhibitor of mTOR activity when the level of the interaction between PLD2 and Rheb decreases compared with that in other sample cells without contacting with the compound.

Another aspect of the present invention is to provide the amino acid sequence from position 476 to position 612 of full-length PLD2 as a target for screening of an agent of treating mTOR-related metabolic diseases may include cancer, diabetes, obesity, hamartoma syndrome including tuberous sclerosis complex, Peutz-Jeghers syndrome, Cowden disease, Proteus syndrome, tissue/organ hypertrophy including cardiac hypertrophy, etc.

Still other aspect of the present invention is to provide methods and compositions for treating mTOR-related metabolic diseases by inhibiting mTOR activity.

The method of treating mTOR-related metabolic diseases may be conducted by inhibiting one or more steps among the steps of:

1) binding of Rheb to mTOR through PLD2 by interaction between PLD2 and Rheb;

2) movement of PA produced from PLD2 near mTOR, to increase the level of PA near mTOR; and 3) binding of Rheb to mTOR due to the increase of PA near mTOR, to activate the mTOR kinase activity.

The composition may contain an effective amount of an inhibitor of mTOR as an active ingredient.

The mTOR-related metabolic diseases may include cancer, diabetes, obesity, hamartoma syndrome including tuberous sclerosis complex, Peutz-Jeghers syndrome, Cowden disease, Proteus syndrome, tissue/organ hypertrophy including cardiac hypertrophy, etc.

DETAILED DESCRIPTION OF THE PREFERRED EMBODIMENTS

Figure 1:
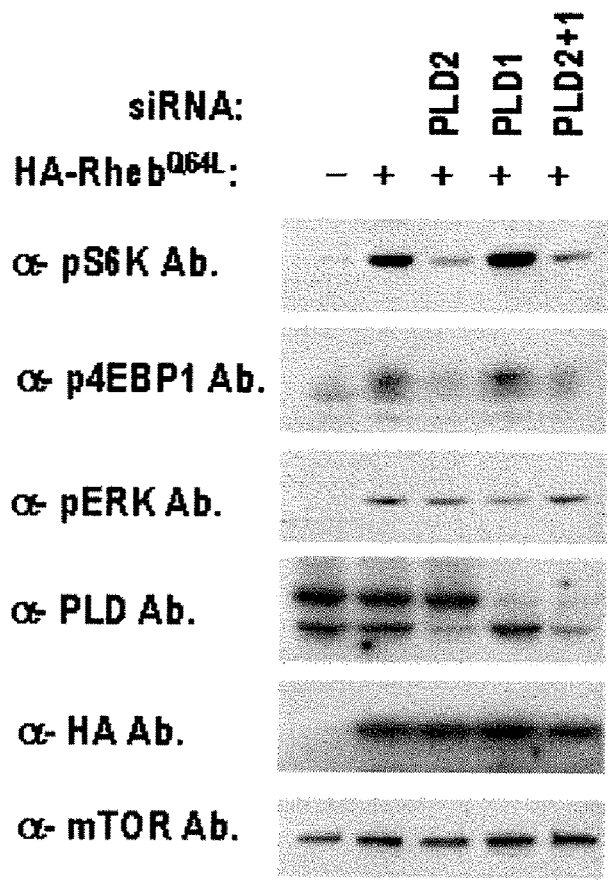
FIG. 1 shows the immunoblotting results from knockdown PLD1 and/or PLD2.

A more complete appreciation of the invention, and many of the attendant advantages thereof, will be readily apparent as the same becomes better understood by reference to the following detailed description.

The inventors speculate that; the mTOR/raptor/PLD2/Rheb complex is stabilized in leucine-rich conditions, PLD2 is activated by Rheb binding, generated PA increases Rheb binding to mTOR, and that finally mTOR is activated. The speculations were proved by the experimentations as below, thereby completing the present invention.

The present inventors have been studied the regulatory mechanisms of mTOR signaling, and found the participation of the mTOR complex (mTOR/raptor) containing raptor and GβL in response to upstream signals for the appropriate control of cell growth. These upstream signals derived from insulin and/or nutrients are likely to be mediated by the tuberous sclerosis complex ½ and Rheb. In addition, mTOR requires the lipid second messenger phosphatidic acid (PA) for its activation. The present invention identifies the regulators of mTOR activity, and the physical/functional connections thererbetween, providing further insight into mTOR-related metabolic diseases such as cancer, diabetes obesity, hamartoma syndrome including tuberous sclerosis complex, Peutz-Jeghers syndrome, Cowden disease, Proteus syndrome, tissue/organ hypertrophy including cardiac hypertrophy, etc.

DEFINITION

The term 'mTOR' refers to a mammalian target-of-rapamycin. In the present invention, mTOR may be originated from any mammalians including human and its amino acid sequences according to the source species are well known in the relevant art. In the present invention, the mTOR may originated from any mammalians, for example, *Homo sapiens* (NP 004949), *Drosophila melanogaster* (NP524891), *Caenorhabditis elegans* (Q95Q95), etc. In an embodiment of the present invention, human mTOR having the amino acid sequence of SEQ ID NO: 1 may be used.

The term 'PLD' refers to a phospholipase D, and mammalian PLD isozymes include to classes, PLD1 and PLD2. In the present invention, PLD may be originated from any mammalians including human, and its amino acid sequences according to the source species are well known in the relevant art. In an embodiment of the present invention, PLD1 (NM 030992, originated from *Rattus norvegicus*) having the amino acid sequence of SEQ ID NO: 2, and PLD2 (NM 002663, originated from *Homo sapiens*) having the amino acid sequence of SEQ ID NO: 3 may be used.

The term 'PA' refers to a phosphatidic acid, which is an enzymatic product of PLD. mTOR requires the lipid second messenger phosphatidic acid (PA) for its activation.

The term 'Rheb' refers to a Ras homolog enriched in brain. In the present invention, the Rheb may be originated from any mammalians including human, mouse, etc., and its amino acid sequences according to the source species are well known in the relevant art. In an embodiment of the present invention, the Rheb may be originated from human, and have the amino acid sequence of SEQ ID NO: 4 (Accession No. NP 065812).

The term 'raptor' refers to a regulatory-associated protein of mTOR. In the present invention, the raptor may be originated from any mammalians including human and its amino acid sequences according to the source species are well known in the relevant art. In an embodiment of the present invention, the raptor may be originated from human, and have the amino acid sequence of SEQ ID NO: 5 (Accession No. Q8N122).

An aspect of the present invention is to reveal a mechanism of regulating mTOR activity by PLD and Rheb. More specifically, the mTOR activity may be activated by the steps of
1) binding of Rheb to mTOR through PLD2 by interaction between PLD2 and Rheb;
2) movement of PA produced from PLD2 near mTOR, to increase the level of PA near mTOR; and
3) binding of Rheb to mTOR due to the increase of PA near mTOR, to activate the mTOR kinase activity.

Figure 23:
FIG. 23 shows a working model for the cooperation of PLD2 and Rheb in nutrient-induced mTOR activation, explaining the role of PLD2 in the Rheb activation of mTOR signaling.
Figure 23:
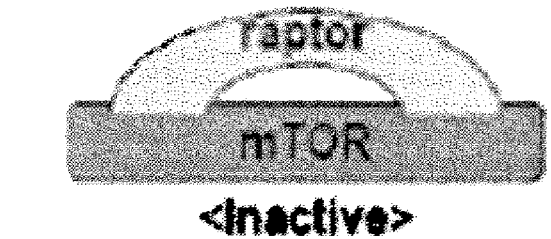
Figure 23:
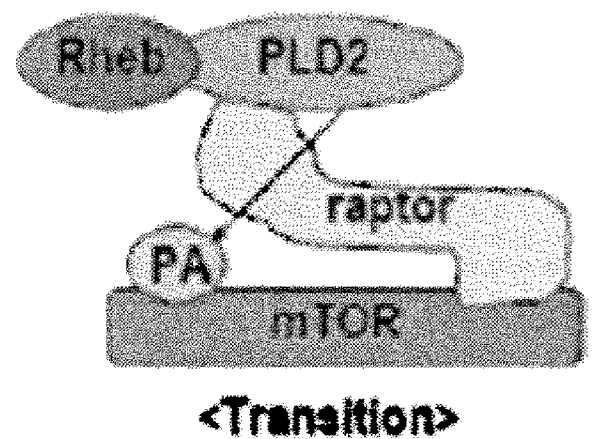

The mechanism is schematically shown in FIG. 23. Therefore, the mTOR activity may be regulated or inhibiting by regulating or inhibiting one or more steps among above steps 1) to 3).

Figure 19:
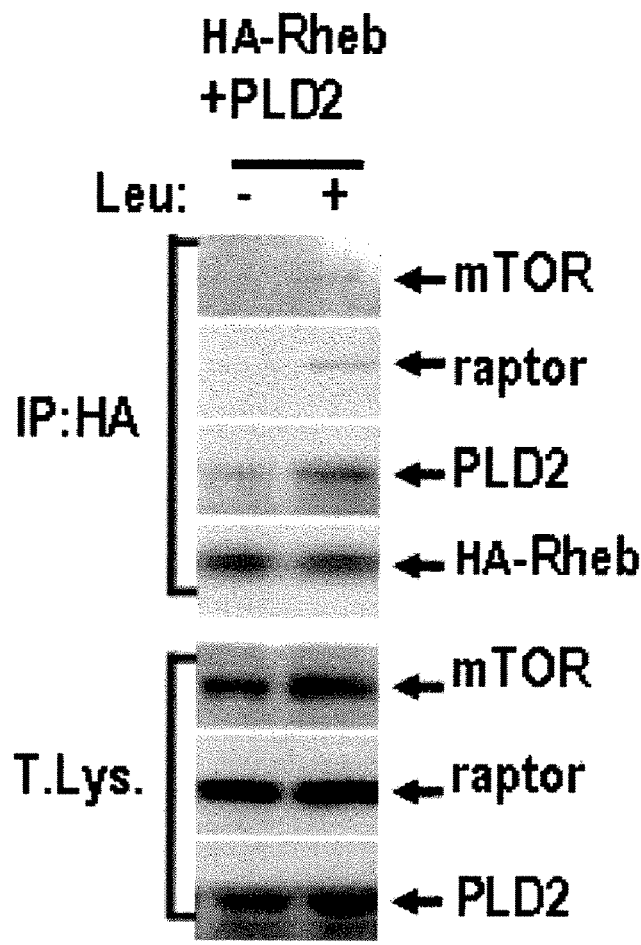
FIG. 19 shows the western blot analysis results in HA-Rheb$^{wt}$/PLD2$^{wt}$ transfectant after leucine treatment.

The binding of Rheb to mTOR may be enhanced by PA in the presence of GTPγS, and thus inhibited by removing PA or GTPγS. Further, the interaction between PLD2 and Rheb may be regulated by nutrient levels, preferably amino acid level, more preferably leucine level, such that this interaction is stabilized under high nutrient conditions and weakened under low nutrient conditions. Therefore, the interaction between PLD2 and Rheb may be inhibited by decreasing the level of nutrients, preferably amino acids, more preferably leucine. As the similar manner, nutrient levels may also regulate the interaction between PLD2 and raptor that mediates the binding of PLD2 to mTOR, allowing a nutrient-dependent mTOR complex composed of mTOR, raptor, PLD2, and Rheb, as shown in FIG. 19.

Based on the above, another aspect of the present invention is to provide a method of regulating mTOR activity by regulating one or more steps among the following steps:

1) binding of Rheb to mTOR through PLD2 by interaction between PLD2 and Rheb;
2) movement of PA produced from PLD2 near mTOR, to increase the level of PA near mTOR; and
3) binding of Rheb to mTOR due to the increase of PA near mTOR, to activate the mTOR kinase activity.

The binding step of Rheb to mTOR may be regulated or inhibited by regulating or inhibiting the interaction between PLD2 and Rheb. The regulation or inhibition of the interaction between PLD2 and Rheb may be conducted by modifying a Rheb binding site of PLD2 and/or a PLD2 binding site of Rheb. In a preferable embodiment of the present invention, the Rheb binding site of PLD2 may comprise the amino acid residues from position 476 to position 612 of full-length PLD2. Therefore, the inhibition of the interaction between PLD2 and Rheb may be conducted by modifying the Rheb binding site of PLD2, and the modification may be deletion of one or more amino acids selected from the amino acid residues from position 476 to position 612 of full-length PLD2, or substitution one or more amino acids from the amino acid residues with other amino acid(s). Alternatively, the modification of Rheb binding site of PLD2 may be conducted by change of pH or temperature, and the like.

The method of inhibiting mTOR according to the present invention results in inhibiting the mTOR' phosphorylation activity on one or more mTOR effectors selected from the group consisting of ribosomal protein S6 kinase 1 (S6K1; e.g., NP 003152, NP 082535, etc.), and 4E-binding protein-1 (4EBP1; e.g., NP 004086).

Another aspect of the present invention is to provide a method of screening inhibitors of mTOR activity. The method of screening inhibitors of mTOR according to the present invention may comprising the steps of:

contacting a candidate compound to a sample cell;
examining the interaction between PLD2 and Rheb by which Rheb is capable of binding to mTOR through PLD2; and
determining the compound as an inhibitor of mTOR activity when the level of the interaction between PLD2 and Rheb decreases compared with that in other sample cells without contacting with the compound.

The sample cell may be any cell capable of expressing PLD2, more preferably PLD2. For example, the sample cell may be selected from the group consisting of a human embryonic kidney (HEK293), a human epithelial ovarian cancer cell (OVCAR-3), COS7 cell, a human cervical cancer (HeLa) cell, a human colon cancer cell (PC-3), a human breast cancer cell (MB231), a human hepatoma (HepG2), a human breast cancer cell (MCF-7), a human T cell leukemia (Jurkat), and the like. The inhibitor of mTOR may be useful in treating mTOR-related metabolic diseases, such as cancer, diabetes, obesity, hamartoma syndrome including tuberous sclerosis complex, Peutz-Jeghers syndrome, Cowden disease, Proteus syndrome, tissue/organ hypertrophy including cardiac hypertrophy, etc. Therefore, the method of the present invention may also used in screening agents of mTOR-related metabolic disease selected from the group consisting of cancer, diabetes, obesity, hamartoma syndrome including tuberous sclerosis complex, Peutz-Jeghers syndrome, Cowden disease, Proteus syndrome, tissue/organ hypertrophy including cardiac hypertrophy, etc.

The interaction between PLD2 and Rheb may be examined by any conventional method, for example by immunoprecipitation, but not limited thereto.

Another aspect of the present invention is to provide the amino acid sequence from position 476 to position 612 of full-length PLD2 as a target polypeptide for screening of an agent of treating mTOR-related metabolic diseases may include cancer, diabetes, obesity, hamartoma syndromes including tuberous sclerosis complex, Peutz-Jeghers syndrome, Cowden disease, Proteus syndrome, tissue/organ hypertrophy including cardiac hypertrophy, etc.

Still other aspect of the present invention is to provide methods and compositions for treating mTOR-related metabolic diseases by inhibiting mTOR activity.

The method of treating mTOR-related metabolic diseases may be conducted by inhibiting one or more steps among the steps of:

1) binding of Rheb to mTOR through PLD2 by interaction between PLD2 and Rheb;
2) movement of PA produced from PLD2 near mTOR, to increase the level of PA near mTOR; and
3) binding of Rheb to mTOR due to the increase of PA near mTOR, to activate the mTOR kinase activity.

More specifically, the method of treating mTOR-related metabolic diseases may be conducted by inhibiting the interaction between PLD2 and Rheb, thereby inhibiting the binding of Rheb to mTOR through PLD2. The treating method may comprise the step of inactivating the Rheb binding domain of PLD2, thereby inhibiting binding of Rheb to mTOR through PLD2. The inactivation of the Rheb binding domain of PLD2 is as aforementioned. Alternatively, the treating method comprises the step of administering an effective amount of an inhibitor of mTOR activity as an active ingredient, wherein the inhibitor of mTOR may be screened by the screening method according to the present invention.

The composition may contain an effective amount of an inhibitor of mTOR as an active ingredient. The inhibitor of mTOR activity may be any material having the activity to inhibit one or more steps among the above three steps. In an embodiment of the present invention, the inhibitor of mTOR activity may be any material having the activity to prevent PLD2 from binding to Rheb, thereby inhibiting the binding of Rheb to mTOR through PLD2, as aforementioned. The inhibitor of mTOR activity may be any material capable of inactivating the Rheb binding domain of PLD2 by various means as aforementioned. Alternatively, the inhibitor of mTOR activity may be a compound screened by the screening method according to the present invention.

The mTOR-related metabolic diseases may include cancer, diabetes, obesity, hamartoma syndrome including tuberous sclerosis complex, Peutz-Jeghers syndrome, Cowden disease, Proteus syndrome, tissue/organ hypertrophy including cardiac hypertrophy, etc.

In the present invention, it is found that PLD2 interacts directly with Rheb and this is important for PLD2 activation. Importantly, this functional connection increases Rheb binding onto the mTOR/raptor complex and the generated PA increases Rheb activation of mTOR kinase activity. Therefore, it may be suggested that PLD2 and Rheb cooperate to regulate a nutrient-induced mTOR signaling.

Based on the above findings, a hypothetic model may be provided in which raptor binding to PLD2, and allowing the accumulation of PA near mTOR through Rheb-induced PLD2 activation, is a prerequisite for mTOR activation by Rheb through the PA-dependent binding of Rheb to mTOR. The model is schematically shown in FIG. 23. Although it is not clear whether the interaction between PLD2 and Rheb is a first-going event for PLD2 binding with raptor, it is also possible that an unidentified signal to mTOR/raptor directly causes PLD2/Rheb to bind raptor since reducing PA generation or PLD2 expression did not modulate the raptor/mTOR interaction.

PLD1 as well as PLD2 activates the mTOR pathway. However, mTOR is likely to interact with PLD2 only, which implies an alternative pathway for the PLD1-dependent activation of the mTOR pathway, possibly through Cdc42/S6K1 signaling. The findings of the present invention also show that the silencing effect of PLD1 on mTOR signaling is completely rescued by PA treatment, but not in the case of silencing PLD2, suggesting an obvious difference between PLD1 and PLD2. The role of PLD1 in mTOR signaling might be mediated by solely PA generation. This also implies that the other PA target upstream of mTOR may be required to mediate this effect. It is possible that PLD2 is under the control of PLD1 since PLD1 signals PLD2 through phosphoinositide 4-phosphate 5 kinase.

PA has been recognized as lipid second messenger generated by mitogenic signals. To identify the downstream effectors, various PA-binding proteins have been found. These include Raf-1, sphingosine kinase 1, phosphatase PP2A, and phosphodiesterases 4A1 as well as mTOR. However, the action mechanism of PA on these effects remains to be addressed. In the present invention, it is of interest to examine the role of PLD2 in the regulation of the other PA binding proteins.

Knowledge about the molecular mechanism by which the mTOR pathway is regulated by cellular nutritional states and how impairment of the pathway leads to metabolic diseases, such as cancer, obesity, diabetes, hamartoma syndrome including tuberous sclerosis complex, Peutz-Jeghers syndrome, Cowden disease, Proteus syndrome, tissue/organ hypertrophy including cardiac hypertrophy, etc., is critically required. The findings of the present invention may be the first step toward attainment of such knowledge. This may be supported by the determination of Rheb-mediated regulation of the mTOR pathway. Interaction of PLD2 with Rheb is stabilized in nutrient-rich condition. Also, interaction of PLD2 with raptor is stabilized in nutrient-rich condition. It may be speculated that these two interactions are a regulatory point for nutrient-induced mTOR activation. Identification of molecular mechanism may provide an important understanding how nutrient impinges on the mTOR complex.

Enhancement of PA production has been reported in various cancer tissues and tumors including prostate cancer and breast cancer. In most cases, this is correlated with overexpression of PLD. However, the mechanism how this is related with tumorigenesis has not been suggested. Our identification of the role of PLD2 in the mTOR signaling suggests the potential molecular mechanism for PLD2-mediated tumorigenesis.

The mTOR signaling has been recognized as an important regulator for metabolic diseases. Insulin receptor substrate-1 (IRS-1) is a newly identified effector for the mTOR signaling. Malfunction of IRS-1 through serine phosphorylation that is mediated by mislocalization and degradation of IRS-1 uncouples normal insulin signaling such as insulin-induced glucose uptake. Uncontrolled regulation of the mTOR signaling by PLD2 and Rheb might be related with mTOR-dependent IRS-1 malfunction.

Taken together, the identification of PLD2 and Rheb as a mediator of mTOR signaling suggests that PLD2 is an important molecular link for nutrient-regulated mTOR signaling, and thereby it presents a novel regulatory point that can be targeted for the treatment of metabolic diseases.

The present invention is further explained in more detail with reference to the following examples. These examples, however, should not be interpreted as limiting the scope of the present invention in any manner.

EXAMPLE 1

Example 1

Preparation of Materials

The enhanced chemiluminescence kit, glutathione-Sepharose 4B and dipalmitoylphosphatidyl[methyl-$^3$H]choline were purchased from Amersham Biosciences. Horseradish peroxidase-conjugated goat anti-rabbit IgG and goat anti-mouse IgA/M/G were from Kirkegaard & Perry Laboratories, Inc. (Gainthersburg, Md.). Polyclonal antibody was raised against PLD as previously described in "Park, J. B. et al. Cardiac phospholipase D2 localizes to sarcolemmal membranes and is inhibited by alpha-actinin in an ADP-ribosylation factor-reversible manner. *J. Biol. Chem.* 275, 21295-21301 (2000)" and "Lee, S. et al. Actin directly interacts with phospholipase D, inhibiting its activity. *J. Biol. Chem.* 276, 28252-28260 (2001)", which are hereby incorporated by reference.

Antibodies against mTOR, pS6K1 (pThr 389), S6K1 and rapamycin were from Cell Signaling Technology (Beverly, Mass.). Antibody for Rheb was from SantaCruz Biotechnology (Santa Cruz, Calif.). Polyclonal raptor antibody was a generously gift from Dr. Do-Hyung Kim (University of Minnesota). Protein A-Sepharose was from RepliGen (Needham, Mass.). CHAPS, leucine and leucine-free RPMI-1640 media were from Sigma (St. Louis, Mo.). Dulbecco's modified Eagle's medium (DMEM) and LipofectAMINE were from Invitrogen (Carlsbad, Calif.). C-6 phosphatidic acid was from Avanti (Alabaster, Ala.) and recombinant 4EBP1 was purchased from Stratagene (La Jolla, Calif.).

Cells and vectors used the following examples were obtained from Invitrogen, unless differently mentioned.

Example 2

Preparation of Plasmids

Mammalian expression vectors for PLD1$^{wt}$, PLD2, PLD2$^{\Delta N184}$, PLD2$^{\Delta N308}$, PLD2$^{K758R}$ and EGFP-PLD2$^{wt}$ and bacterial expression vectors for GST-tagged PLD2 fragments were used as described previously in "Park, J. B. et al. Cardiac phospholipase D2 localizes to sarcolemmal membranes and is inhibited by alpha-actinin in an ADP-ribosylation factor-reversible manner. *J. Biol. Chem.* 275, 21295-21301 (2000)" and "Lee, S. et al. Actin directly interacts with phospholipase D, inhibiting its activity. *J. Biol. Chem.* 276, 28252-28260 (2001)", which are hereby incorporated by reference.

Expression vectors for HA-mTOR$^{wt}$, myc-mTOR$^{wt}$, myc-raptor$^{wt}$, HA-raptor$^{wt}$ and HA-raptor$^{194YDC/AAAmt}$ were gifts from Dr. David M. Sabatini (MIT) (Kim, D. H., et al. mTOR interacts with raptor to form a nutrient-sensitive complex that signals to the cell growth machinery. *Cell* 110, 163-175 (2002), which is hereby incorporated by reference). Mammalian expression vectors for Rheb and bacterial expression vectors for GST-Rheb, GST-Rap1, and GST-R-Ras were kindly provided by Dr. Ariel F. Castro (Indiana University, USA). To introduce the TOS-motif mutation in PLD2, pcDNA3.1(+)/PLD2 containing wild type PLD2 was PCR amplified using the following oligomers; sense (5'GGC CGA GAC CAA GTT TGT TAT CGC3'; SEQ ID NO: 6), antisense (F265A:5'CCA TCG ATC CGC ACG CCG TGC CGT GCC TCC GTG CTC CTT TTC CCC ACT TGC ACC TCA GCG CCA GG3'; SEQ ID NO: 7), antisense (E266R:5'CCA TCG ATC CGC ACG CCG TGC CGT GCC TCC GTG CTC CTT TTC CCC ACT TGC ACC CTA AAG CCA GG3'; SEQ ID NO: 8).

DNA fragments generated by PCR and pcDNA3.1(+)/PLD2(WT) were treated with XhoI and Cla I. His-Rheb was generated by using a standard PCR cloning strategy using myc-Rheb as a template. PCR fragments of Rheb were subcloned in frame into the BamHI/EcoRI sites of pRSET-B vector. All mutant constructs were verified by DNA sequencing. Mammalian expression vectors for myc-S6K1, myc-4EBP1 and HA-raptor fragments (HA-raptor$^{1-646}$, HA-raptor$^{1020-1335}$, HA-raptor$^{647-1335}$, HA-raptor$^{647-1019}$) were generous gifts from Dr. David M. Sabatini (MIT). N-terminal deleted PLD2 fragments were as described previously in "Park, J. B. et al. Cardiac phospholipase D2 localizes to sarcolemmal membranes and is inhibited by alpha-actinin in an ADP-ribosylation factor-reversible manner. *J. Biol. Chem.* 275, 21295-21301 (2000)", which is hereby incorporated by reference. GST-fusion PLD2 fragments used for bacterial expression were prepared as previously described in "Park, J. B. et al. Cardiac phospholipase D2 localizes to sarcolemmal membranes and is inhibited by alpha-actinin in an ADP-ribosylation factor-reversible manner. *J. Biol. Chem.* 275, 21295-21301 (2000)" and "Lee, S. et al. Actin directly interacts with phospholipase D, inhibiting its activity. *J. Biol. Chem.* 276, 28252-28260 (2001)", which are hereby incorporated by reference.

Example 3

RNA interference

Pairs of 21-nucleotide sense and antisense RNA oligomers were synthesized and annealed by Dharmacon Research, Inc. (Lafayette, Colo.) as described in "Ha, S. H., Kim, D. H., Kim, I. S., Kim, J. H., Lee, M. N., Lee, H. J., Kim, J. H., Jang, S. K., Suh, P. G., Ryu, S. H. PLD2 forms a functional complex with mTOR/raptor to transduce mitogenic signals. *Cell. Signal.* 18 (2006) 2283-2291", which is hereby incorporated by reference.

The oligonucleotides used for PLD2 were: sense, 5'-AAG AGO UGG CUG GUG GUG AAG-3' (SEQ ID NO: 9) and antisense, 5'-CUU CAC CAC CAG CCA CCU CUU-3' (SEQ ID NO: 10), which correspond to human PLD2 coding nucleotides 703-723. All siRNA sequences were subjected to BLAST in the NCBI database and complete matches were only found for PLD2 sequences. Luciferase GL2 duplex was purchased from Dharmacon Research, Inc. and was used as a negative control. The shRNA-encoding lentiviral plasmid was constructed to target the human Rheb mRNA sequence of 5'-GAGGACACTGGGAATATATTC-3' (SEQ ID NO: 11) using the pLKO vector29.

For add-back experiment for PLD2 silencing, three residues of human PLD2 cDNA (nucleotides 703-723 of PLD2; AAGAGGTGGCTGGTGGTGAAG, SEQ ID NO: 12) are substituted to AAGAGATGGCTAGTAGTGAAG for addback mutants of PLD2. This mutation is silencing mutations. This gene is subcloned into mammalian expression vector pcDNA3.1 (Invitrogen) and digested with restriction enzymes KpnI and XbaI. These mutations are confirmed through nucleotide sequence analysis.

Example 4

Cell Culture and Plasmid/siRNA Transfection

COS7 cells (ATCC, CRL-1651) were maintained in a 5% $CO_2$ humidified atmosphere at 37° C. and fed DMEM supplemented with 10% bovine calf serum (HyClone). HEK293 cells (ATCC: CRL-1573) were fed DMEM supplemented with 10% fetal bovine serum (HyClone). Cells grown on tissue culture dishes were transiently transfected using LipofectAMINE, as described in "Park, J. B. et al. Cardiac phospholipase D2 localizes to sarcolemmal membranes and is inhibited by alpha-actinin in an ADP-ribosylation factor-reversible manner. *J. Biol. Chem.* 275, 21295-21301 (2000)" and "Lee, S. et al. Actin directly interacts with phospholipase D, inhibiting its activity. *J. Biol. Chem.* 276, 28252-28260 (2001)", which are hereby incorporated by reference. Cells were allowed to express the recombinant proteins for 24 hr after transfection and then deprived of serum for additional 24 hr. The cells were then subjected to leucine deprivation, co-immunoprecipitation, or GST pull-down analysis. Leucine deprivation was performed as previously described 10 with minor modification. Briefly, cells were deprived of serum first for 24 hrs and then subjected to leucine deprivation in leucine-free RPMI 1640 medium.

Example 5

Co-Immunoprecipitation

After harvesting COS7 cells, total extracts were prepared by brief sonication in ice-cold lysis buffer (40 mM HEPES pH7.5, 120 mM NaCl, 1 mM EDTA, 10 mM pyrophosphate, 10 mM glycerophosphate, 50 mM NaF, 1.5 mM $Na_3VO_4$, 0.5% CHAPS, 1 mM PMSF, protease inhibitor cocktails). Clarified extracts were mixed with 2 μg of the respective antibodies. Then protein A-Sepharose beads were added to isolate the antibody complex. After four washings with lysis buffer, the final immunoprecipitates were washed once with wash buffer (50 mM HEPES pH7.5, 150 mM NaCl), and then subjected to SDS-PAGE using Hyperfilm (Amersham Pharmacia Biotech), nitrocellulose membranes (Watmann), Power supply (Amersham Pharmacia Biotech), Electrophoretic Transfer unit (Hoefer Scientific Instruments), and ECL™ (Amersham Pharmacia Biotech).

Example 6

In Vitro Binding Analysis

GST fusion proteins (PLD2 fragments, GST-Rheb, GST-Rap1, and GST-R-Ras) expressed in *E. coli* (Invitrogen) were isolated using glutathione-Sepharose 4B beads and then incubated with cell lysates expressing either PLD2 or HA-Rheb$^{wt}$ ectopically. After incubation at 4° C. for 2 hr, the beads were washed and then subjected to SDS-PAGE. *E. coli* and COS7 cells were lysed with the lysis buffer used for the co-immunoprecipitation. Hexa-histidine (His6)-tagged PLD2 was purified from detergent extracts of baculovirus-infected Sf9 cells (Invitrogen) by chelating Sepharose affinity column chromatography, as previously described in Lee, S. et al. Actin directly interacts with phospholipase D, inhibiting its activity. *J. Biol. Chem.* 276, 28252-28260 (2001), which is hereby incorporated by reference. As indicated, recombinant proteins (GST-Rheb, GST-2F3, GST-2F2, and His-Rheb) were further eluted after affinity purification using either GSH or nickel. In vitro binding analysis was done in ice-cold lysis buffer (as used for the co-immunoprecipitation but including 10% glycerol).

Example 7

Western Blot Analysis

Proteins were separated by SDS-PAGE on 8-16% gradient gels, and the separated proteins were transferred onto nitrocellulose membranes and blocked with TTBS buffer (10 mM Tris-HCl, pH 7.6, 150 mM NaCl, and 0.05% Tween-20) containing 5% skimmed milk powder. The SDS-PAGE was performed using Hyperfilm (Amersham Pharmacia Biotech), nitrocellulose membranes (Watmann), Power supply (Amersham Pharmacia Biotech), Electrophoretic Transfer unit (Hoefer Scientific Instruments), and ECL™ (Amersham Pharmacia Biotech). Membranes were then incubated with primary antibody at the concentration recommended by the manufacturer for 4 hr at room temperature. Unbound antibody was washed away with TTBS buffer. Membranes were subsequently incubated with horseradish peroxidase-conjugated secondary antibody for 1 hr at room temperature, washed five times with TTBS buffer, and developed using an ECL system.

Example 8

In Vivo PLD Assay

In vivo PLD activity was assayed by measuring the formation of phosphatidyl-butanol as described in "Lee, S. et al. Actin directly interacts with phospholipase D, inhibiting its activity. *J. Biol. Chem.* 276, 28252-28260 (2001)" and "Ha, S. H., Kim, D. H., Kim, I. S., Kim, J. H., Lee, M. N., Lee, H. J., Kim, J. H., Jang, S. K., Suh, P. G., Ryu, S. H. PLD2 forms a functional complex with mTOR/raptor to transduce mitogenic signals. *Cell. Signal.* 18 (2006) 2283-2291", which are hereby incorporated by reference.

In brief, cells were loaded with [$^3$H]myristic acid (2 µCi/ml) for 8 hr and then washed twice with DMEM. Labeled cells were incubated with 0.4% butanol for 10 min to measure basal PLD activity. Total lipids were extracted with 1.2 ml of methanol:1M NaCl:chloroform (1:1:1 by volume) and then separated by thin-layer chromatography on silica gel plates. The amount of [$^3$H]phosphatidyl-butanol formed was expressed as a percentage of total [$^3$H]lipid to account for cell labeling efficiency differences.

Example 9

In Vitro Kinase Assay for mTOR Activity

Recombinant myc-mTOR was expressed with the indicated proteins and then immunoprecipitated using anti-myc antibody, as previously described in "Lee, S. et al. Actin directly interacts with phospholipase D, inhibiting its activity. *J. Biol. Chem.* 276, 28252-28260 (2001)" and "Ha, S. H., Kim, D. H., Kim, I. S., Kim, J. H., Lee, M. N., Lee, H. J., Kim, J. H., Jang, S. K., Suh, P. G., Ryu, S. H. PLD2 forms a functional complex with mTOR/raptor to transduce mitogenic signals. *Cell. Signal.* 18 (2006) 2283-2291", which are hereby incorporated by reference. Recombinant 4EBP1 (Stratagen) was used as a substrate for in vitro kinase assays. Activities were measured using anti-phospho-4EBP1 antibody (phosphor-37/46). The kinase assay was performed by mixing buffer containing 25 mM Hepes pH7.4, 50 mM KCl, 10 mM $MgCl_2$, 4 mM $MnCl_2$, 20% glycerol, 2 mM DTT, 0.1 mM ATP, 1 µg 4EBP1 with the indicated immunoprecipitates and then incubated at 30° C. for 15 min.

Example 10

Examination of Interrelation Between PLD2 and Rheb

The investigation of the present invention was initiated to test whether functional and/or physical connections between PLD and Rheb exist because no report to date has addressed their interrelationships. Also, it has been reported that Rheb activates mTOR via unknown mechanism.

To examine the potential involvement of PLD in Rheb-mediated mTOR activation, each PLD isozyme (mammals have two, PLD1 and PLD2, which share about 50% identity) was silenced by specific siRNA. HA-Rheb$^{Q64L}$ was expressed in HEK293 cells with the indicated siRNAs. Resulting lysates were immunoblotted with the antibodies in FIG. 1. The obtained results were shown in FIG. 1, showing that knock-down of PLD2 specifically reduced the phosphorylations of S6K1 and 4EBP1, which have been well-defined mTOR substrates. It is likely that the involvement of PLD2 in Rheb-induced mTOR activation is specific since the phosphorylation of extracellular signal-regulated protein kinase (ERK) induced by Rheb was not modulated by knock-down of either PLD1 or PLD2 or both.

Figure 2:
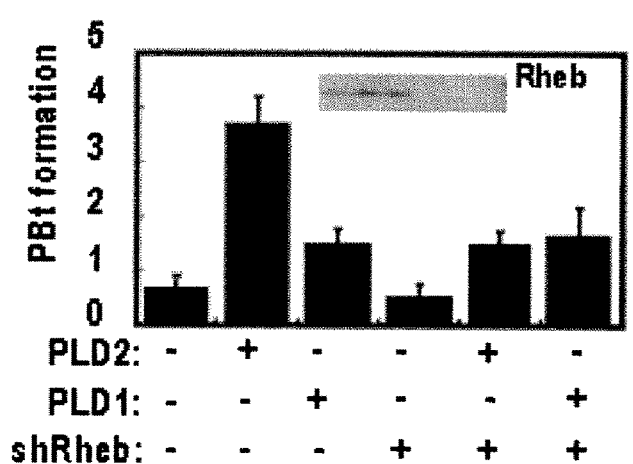
FIG. 2 shows the level of posphatidyl-butanol formation (PBt formation) from knockdown PLD1, PLD2, and/or Rheb.

As an opposite direction, to determine whether Rheb is required for PA generation, the effect of Rheb on the activities of PLD isozymes was tested. PLD2 or PLD1 was transfected into COS7 cells with shRNA against Rheb. After 48 hr, cells were deprived of serum for 20 hr, labeled with [$^3$H]myristic acid for 4 hr, and subjected to PLD assay, as described in Examples 1-8. Posphatidyl-butanol formation (PBt formation) were measured and shown in FIG. 2. Silencing of Rheb was verified by Western blot analysis and presented within graph of FIG. 2 indicated as shRheb. The result in FIG. 2 reveals that effect of Rheb was restricted to PLD2 by Rheb silencing, suggesting that Rheb is required for PLD2 specifically. These results demonstrate that both PLD2 and Rheb are required for mTOR activation.

Example 11

Direction of Interaction Between PLD2 and Rheb

Figure 3:
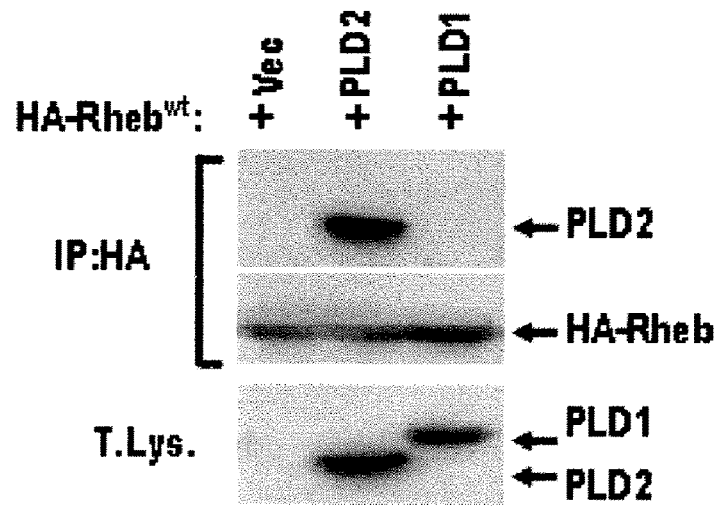
FIG. 3 shows the results of western blot analysis from HA-Rheb$^{wt}$ transfected with PLD2 or PLD1.
Figure 5:
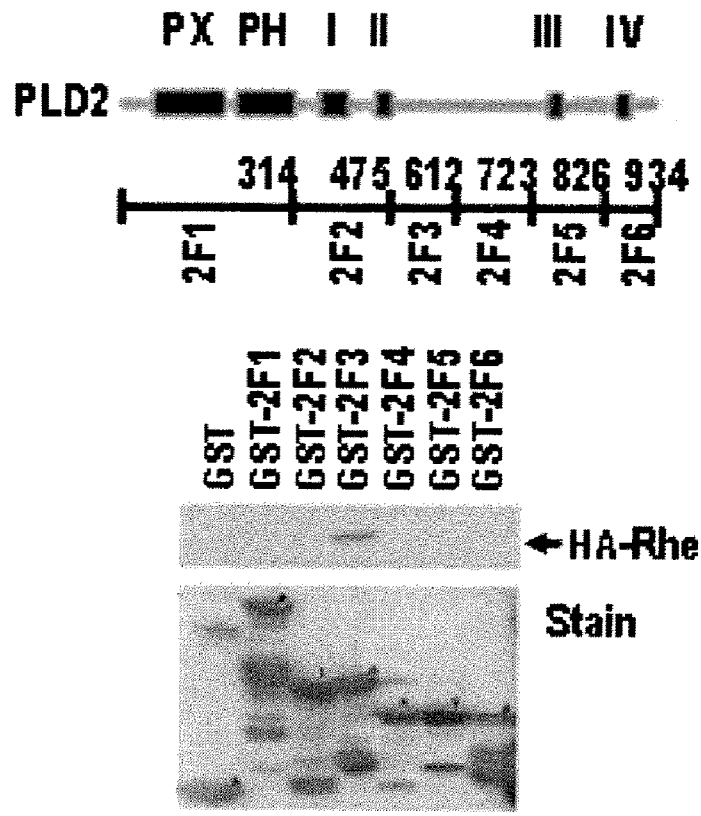
FIG. 5 shows a schematic view of the PLD2 fragments (upper panel) and the result of GST-pull down analysis using the PLD2 fragments (lower panel).

The physical connection between PLD2 and Rheb to support their functional connection was tested. HA-Rheb$^{wt}$ with either PLD2 or PLD1 in COS7 cells was overexpressed. The levels of PLD isozymes in HA-immunoprecipates were examined. HA-Rheb$^{wt}$ was transfected with PLD2 or PLD1 and resulting lysates were immunoprecipitated with anti-HA antibody. Western blot analysis was performed as described above to detect bound PLD isozymes in HA-immunoprecipitates. The obtained results were shown in FIG. 3 (IP; immunoprecipitation, T.Lys.; Total lysates). As shown in FIG. 5, PLD2 was found, but not PLD1, in HA immunoprecipitates. The GTP- or GDP-forms of Rheb did not show any preference in terms of interaction with PLD2 in cells or in vitro.

Figure 4:
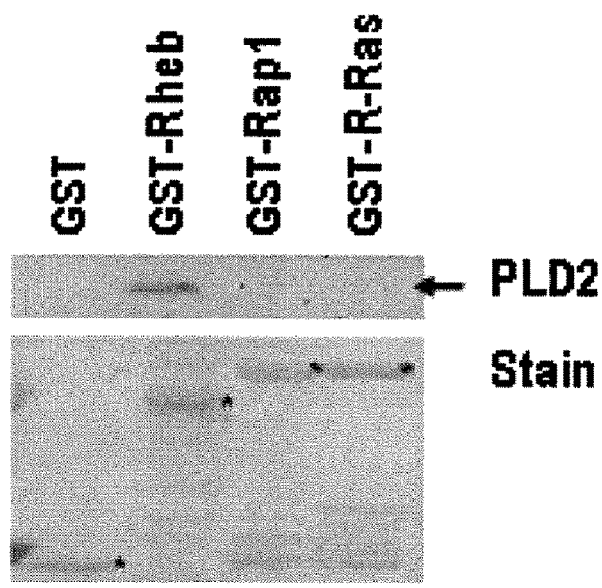
FIG. 4 shows the results of GST-pull down analysis with PLD2-expressing cell lysates.

The interaction between PLD2 and Rheb was further tested by GST-pull down analysis as described in Example 6. GST-fusion proteins (GST-Rheb, GST-Rap1 and GST-R-Ras) were expressed and then used for GST-pull down analysis with PLD2-expressing cell lysates. The obtained results were shown in FIG. 4, wherein GST-fusion proteins are denoted by asterisks. FIG. 4 shows that PLD2 interacted with GST-Rheb but not with GST-Ras or GST-Rap1. This interaction was specific to PLD2, as PLD1 was not detected in the same pull-down experiments.

To understand how Rheb interacts with PLD2, a series of truncated PLD2 mutants were prepared and their abilities to bind Rheb were tested by GST-pull down analysis as described in Example 6. The obtained results were shown in FIG. 5, wherein the upper panel is a schematic view of the PLD2 fragments used, and the lower panel shows the result of GST-pull down analysis. As shown in FIG. 5, the Rheb docking site on PLD2 was mapped to a region encompassing amino acid 476-612 of full-length Rheb.

Figure 6:
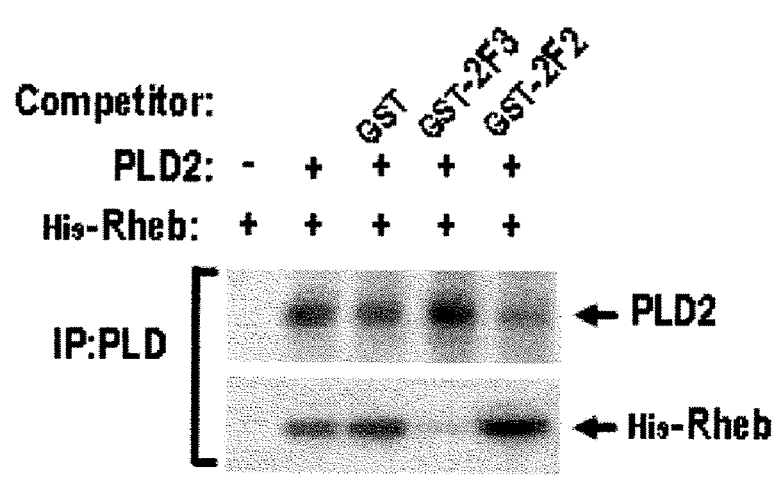
FIG. 6 shows the results of western blot analysis using PLD2 fragments, 2F3 and 2F2.

To reveal whether their interaction is direct, purified PLD2 and Rheb were reconstituted for in vitro binding analysis as described above. Recombinant PLD2 and His-Rheb were expressed and purified from Sf9 cells and *E. coli*, respectively. In addition, GST, GST-2F3 (amino acids 476-612 of PLD2), and GST-2F2 (amino acids 315-475 of PLD2) were expressed and purified from *E. coli* using GSH-Sepharose beads. The purified GST-fusion proteins (40 nM each) were mixed with protein mixture containing PLD2 and His-Rheb and then anti-PLD antibody and protein A-agarose bead were added to precipitate PLD2 from the protein mixture. Bound proteins were detected by Western blotting as described above. The obtained results were shown in FIG. 6. As shown in FIG. 6, their interaction was direct through amino acid 476-612 (designated as 2F3 in FIG. 5) of PLD2. Taken together, Rheb and PLD2 are connected both physically and functionally, and their interaction results in PA generation.

Example 12

Investigation of PLD2 Mediates Rheb Binding to the mTOR Complex and its Effect on Rheb Activation of mTOR Based on the inventors' previous finding that the Rheb/PLD2 complex is related to the PLD2/raptor/mTOR complex (Ha, S. H., Kim, D. H., Kim, I. S., Kim, J. H., Lee, M. N., Lee, H. J., Kim, J. H., Jang, S. K., Suh, P. G., Ryu, S. H. PLD2 forms a functional complex with mTOR/raptor to transduce mitogenic signals. *Cell. Signal.* 18 (2006) 2283-2291, which is hereby incorporated by reference) and the results obtained above, this example examined whether mTOR complex contains raptor, PLD2, and Rheb.

Figure 7:
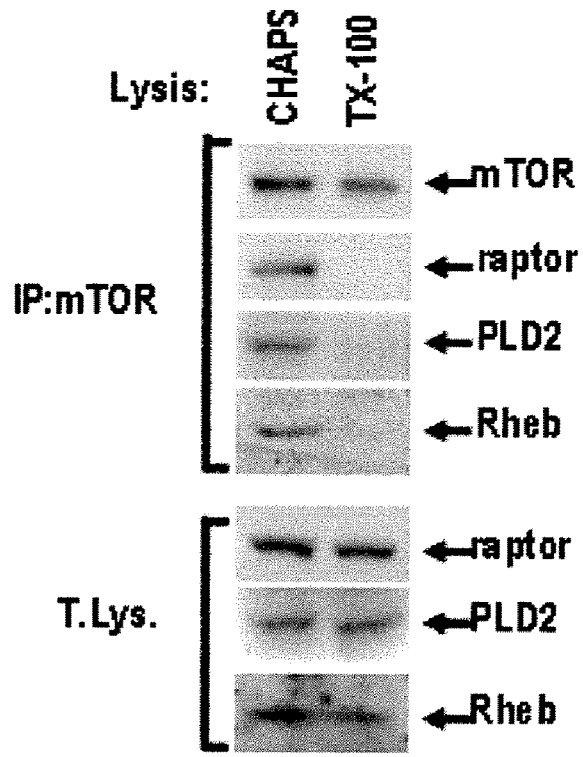
FIG. 7 shows the results of co-IP (immunoprecipitation) against anti-mTOR antibody.

COS7 cell lysates were prepared using different lysis conditions, CHAPS and Triton X-100, and then subjected to co-IP against anti-mTOR antibody described above. The obtained results were shown in FIG. 7. As shown in FIG. 7, raptor, PLD2 and Rheb were found in the mTOR complex.

Figure 8:
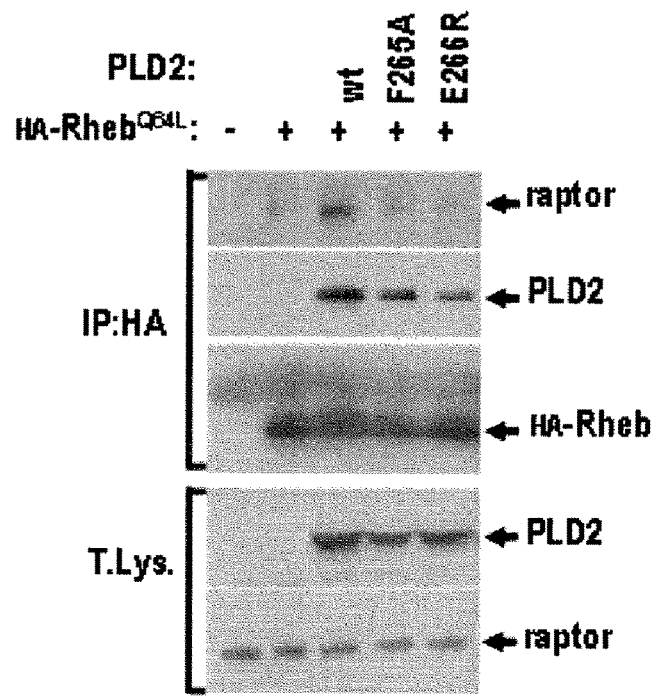
FIG. 8 shows the levels of bound raptor and PLD2 detected by Western blotting using various PLD mutants.

Rheb was found to bind raptor complex, and this interaction was enhanced by PLD2 in a TOS motif-dependent manner as shown in FIG. 8. HA-Rheb$^{Q64L}$ was transfected with the indicated PLD2 mutants into COS7 cells and the resulting lysates were immunoprecipitated with anti-HA antibody. Levels of bound raptor and PLD2 were detected by Western blotting. The obtained results shown in FIG. 8 suggest the importance of PLD2 as a molecular bridge between Rheb and mTOR complex.

Figure 9:
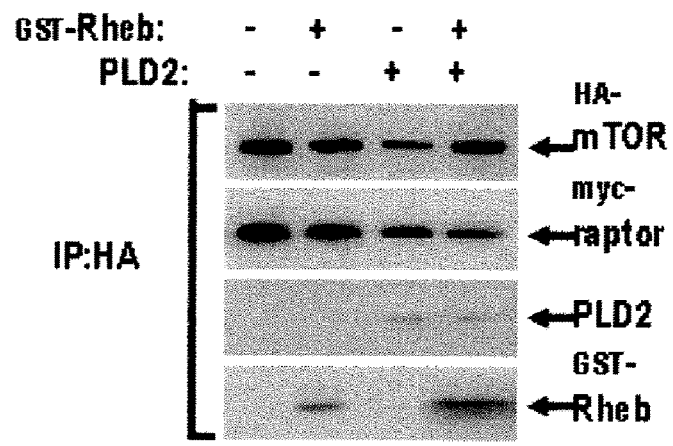
FIG. 9 shows the IP results against anti-HA antibody in mTOR/raptor complex.

The enhanced binding of Rheb with mTOR complex was also confirmed by in vitro binding analysis with purified mTOR immunoprecipitates as described above and the results were shown FIG. 9. After transfection of HA-mTOR$^{wt}$ and myc-raptor$^{wt}$, the mTOR/raptor complex was immunoprecipitated with anti-HA antibody. The resulting immunoprecipitate was further incubated for in vitro binding analysis with purified PLD2 and GST-Rheb (40 nM) as indicated, in the presence of 100 μM GTPγS. After incubation for 2 hr, immunoprecipitates were rewashed and Western blotted.

Figure 10:
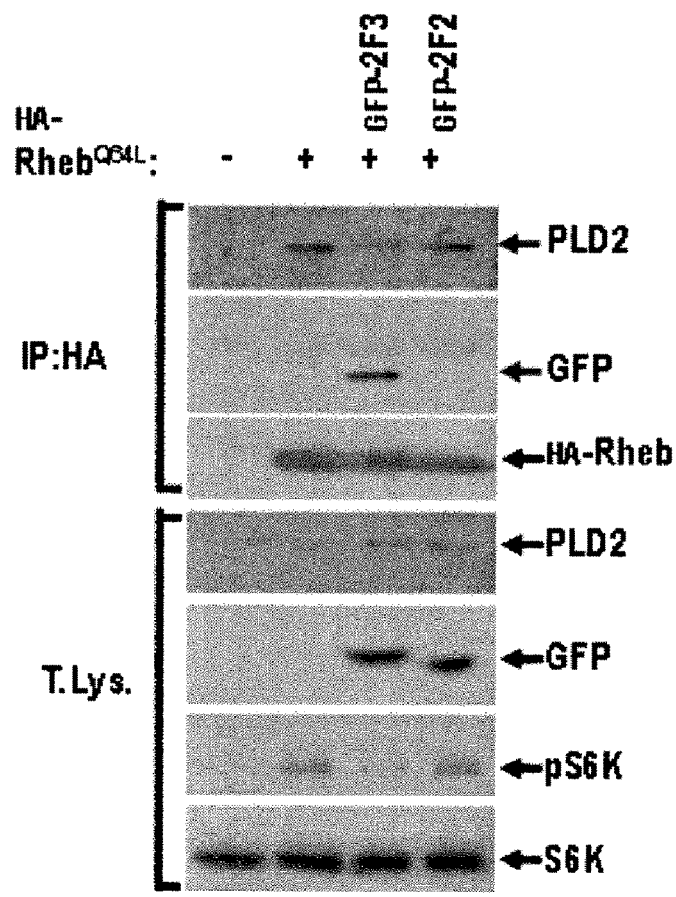
FIG. 10 shows the co-IP analysis results against anti-HA antibody in HA-Rheb$^{Q64L}$ transfected with GFP-2F3 or GFP-2F2.

The importance of PLD2 as a physical link in mTOR signaling was further highlighted by PLD silencing followed by PA treatment, which was shown to increase mTOR activity in cells as reported in the inventors' previous report (Ha, S. H., Kim, D. H., Kim, I. S., Kim, J. H., Lee, M. N., Lee, H. J., Kim, J. H., Jang, S. K., Suh, P. G., Ryu, S. H. PLD2 forms a functional complex with mTOR/raptor to transduce mitogenic signals. *Cell. Signal.* 18 (2006) 2283-2291, which is hereby incorporated by reference). It has been reported that, interestingly, PA could no longer activate mTOR pathway when PLD2 expression was lowered. However, PA could rescue mTOR activity when PLD1 expression was lowered, suggesting the importance of PLD2 itself to activate mTOR kinase activity. The importance of the link between PLD2 and Rheb was tested using small fragments, 2F3 and 2F2, derived from the Rheb binding region of PLD2. After transfecting HA-Rheb$^{Q64L}$ with GFP-2F3 or GFP-2F2, cells were deprived of serum and then co-IP analyses were performed using anti-HA antibody as described above. The obtained results were shown in FIG. 10. As shown in FIG. 10 as well as FIG. 5, Rheb interaction with PLD2 in cells was abrogated by GFP-2F3, but not by GFP-2F2. This is well correlated with decreased S6K1 phosphorylation by GFP-2F3 overexpression in Rheb-overexpressed cells (FIG. 10).

Figure 11:
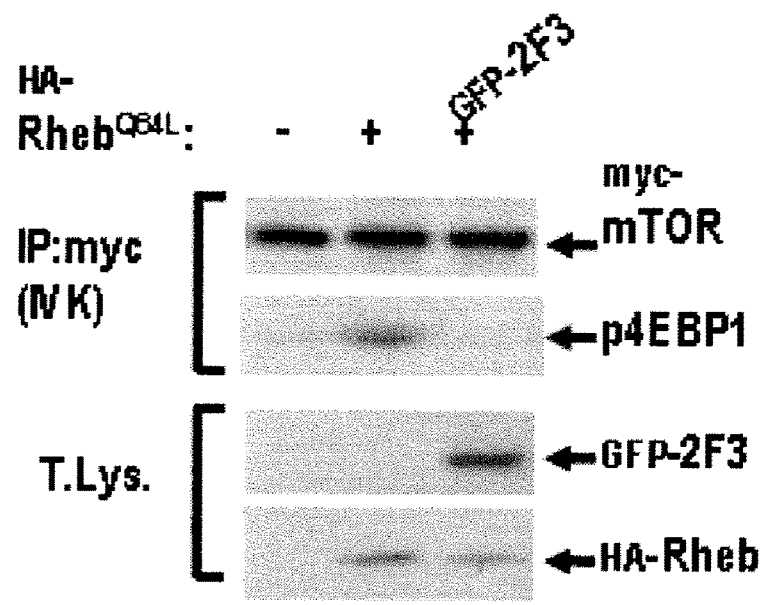
FIG. 11 shows the results of mTOR kinase assays using anti-myc immunoprecipitates.

To test whether Rheb-induced mTOR kinase activity is also downregulated by GFP-2F3 overexpression, the following test was performed. After transfecting HA-Rheb$^{Q64L}$, GFP-2F3 and myc-mTOR, in vitro mTOR kinase assays were performed using anti-myc immunoprecipitates as described above. The results were shown in FIG. 11. As confirmed in FIG. 11, Rheb-induced mTOR kinase activity was also downregulated by GFP-2F3 overexpression, suggesting the importance of Rheb/PLD2 binding for Rheb-induced mTOR activation. This raised the possibility that the enzymatic activation of PLD2 together with its physical link is important for the Rheb activation of mTOR.

Example 13

Role of PA in Rheb Activity to Activate mTOR Kinase Activity

The mechanism by which PA activates mTOR in cells was not revealed by an earlier study (Kim, D. H., et al. mTOR interacts with raptor to form a nutrient-sensitive complex that signals to the cell growth machinery. *Cell* 110, 163-175 (2002), which incorporated herein as a reference). Only a conformational change of mTOR or its specific recruitment of an upstream regulator was suggested.

Figure 12:
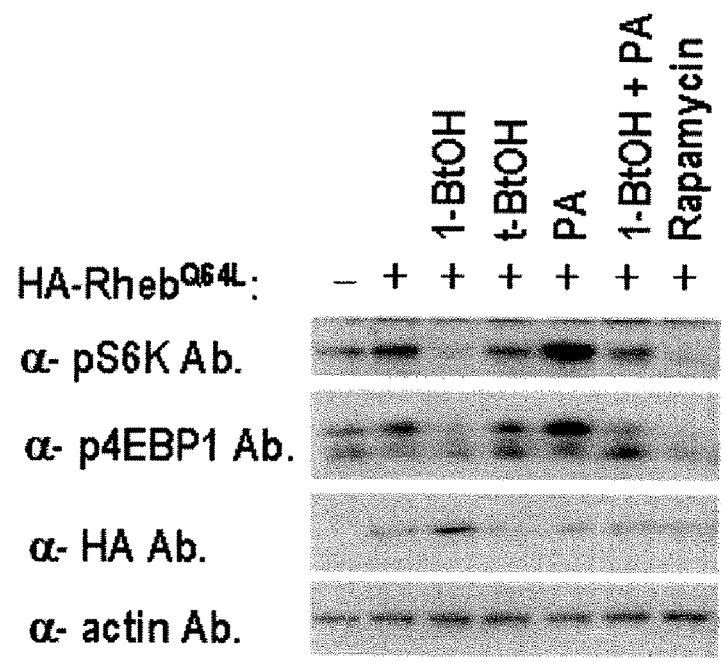
FIG. 12 shows the IP analysis results obtained in the transfected HA-RhebQ64L treated with 1-butanol, t-butanol, phosphatidic acid, and rapamycin, respectively.
Figure 13:
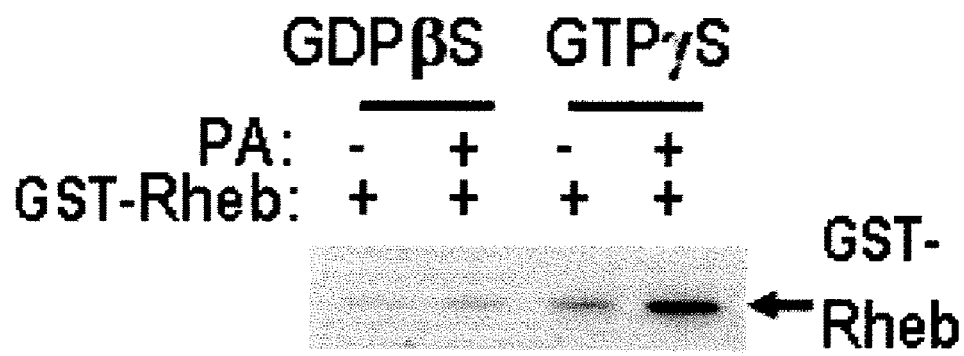
FIG. 13 shows IP analysis results obtained from the binding of GST-Rheb to mTOR complex by PA in the presence of GDPβS or GTPγS.

This example examined the speculation that PA could increase Rheb/mTOR binding and activate mTOR through PA-dependent conformational change of mTOR. After transfection of HA-Rheb$^{Q64L}$, cells were deprived of serum for 24 hr, then treated with 1-butanol (1-BtOH, 0.4%), t-butanol (t-BtOH, 0.4%), phosphatidic acid (C-6 PA, 100 uM), and rapamycin (20 nM), respectively. The obtained results were shown in FIG. 12. The speculation was further forced because the results shown in FIG. 12 shows that PA is essentially required for Rheb to activate the mTOR signaling, as verified in rescue experiment from 1-butanol-treated cells by PA. Also, it was observed that the interaction between mTOR and Rheb was attenuated in 1-butanol-treated cells, which suggested the importance of PA production for their interaction.

mTOR/raptor/PLD2 was purified by immunoprecipitation, and then used as in vitro bait for purified GST-Rheb together with PA. HA-mTOR, myc-raptor, and PLD2 were transfected and resulting lysates were immunoprecipitated with anti-HA antibody. The resulting immunoprecipitates were used for in vitro binding analysis with purified GST-Rheb (40 nM), PA (10 μM), GDPβS (100 μM), or GTPγS (100 μM). The obtained results were shown in FIG. 13. As shown in FIG. 13, PA increased GST-Rheb binding to mTOR complex in the presence of GTPγS.

Figure 14:
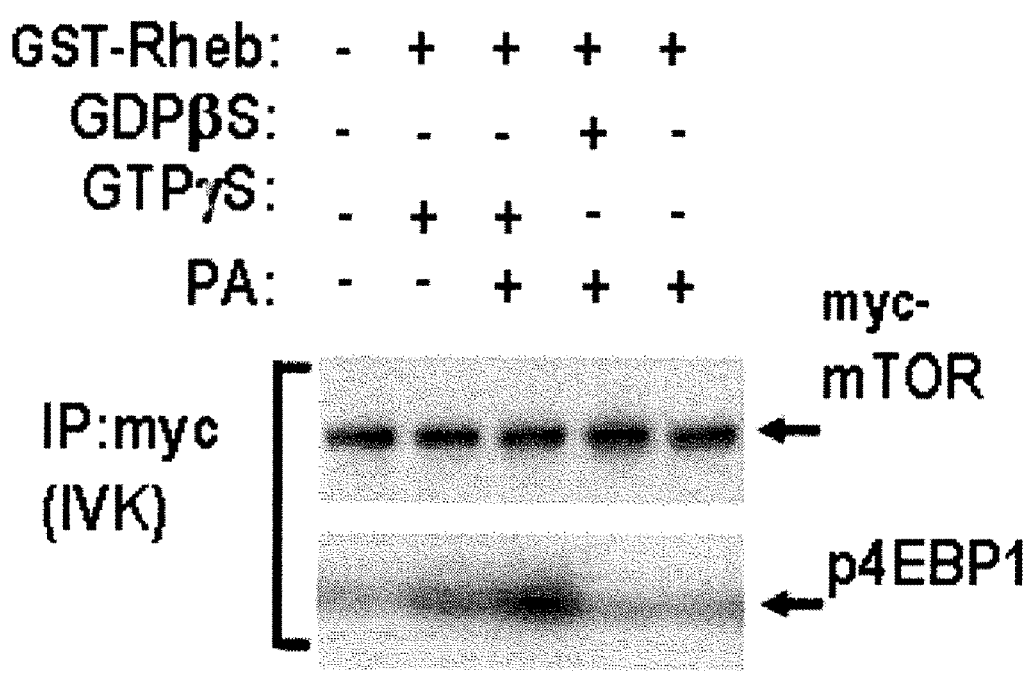
FIG. 14 shows the results of in vitro mTOR kinase assay for myc-mTOR transfectant.
Figure 15:
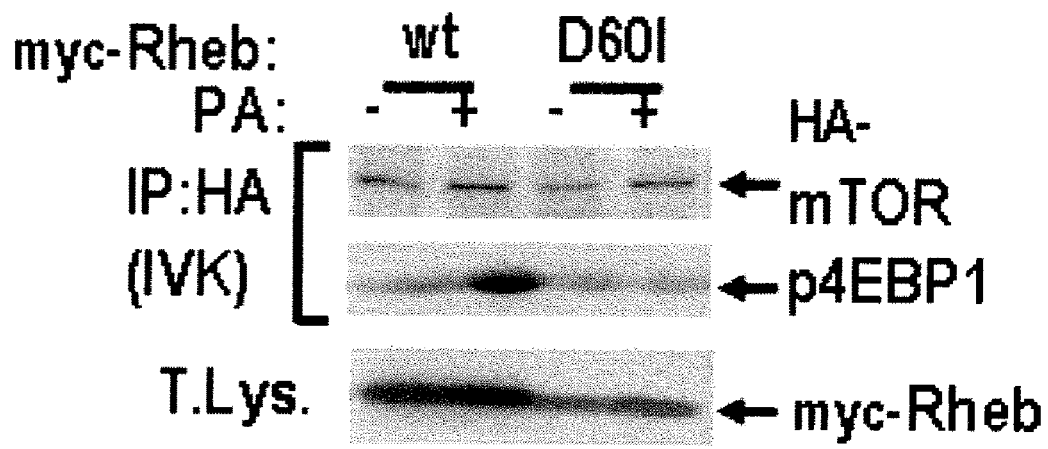
FIG. 15 shows the results of in vitro mTOR kinase assay in COS7 cells transfected with HA-mTOR and myc-Rheb$^{wt}$ or myc-Rheb$^{D60I}$.

This enhanced binding was correlated with mTOR activation both in vitro and in vivo, as shown in FIGS. 14 and 15. Myc-mTOR, HA-raptor and PLD2 were transfected into HEK293 cells and resulting lysates were immunoprecipitated with anti-myc antibody. The resulting immunoprecipitate was used for in vitro mTOR kinase assay. The obtained results were shown in FIG. 14 (IVK: in vitro kinase assay). HA-mTOR$^{wt}$ and myc-Rheb$^{wt}$ or myc-Rheb$^{D60I}$ were transfected into COS7 cells and allowed to express for 24 hr. After 24 serum starvation, 100 μM PA was treated to cells and the resulting lysates were subjected to in vitro kinase assay for mTOR. The obtained results were shown in FIG. 15.

Taken together, the above results suggest that PLD2 provides a physical link between Rheb and the mTOR complex, and that, as a result, the PA generated in the proximity of the mTOR complex increases Rheb/mTOR complex binding, which result in mTOR activation.

Example 14

Investigation of Nutrient Dependent PLD2 Activation

Previously, the inventors suggested that both the PLD2/raptor interaction and the enzymatic activity of PLD2 are required for mTOR pathway stimulation (Ha, S. H., Kim, D. H., Kim, I. S., Kim, J. H., Lee, M. N., Lee, H. J., Kim, J. H., Jang, S. K., Suh, P. G., Ryu, S. H. PLD2 forms a functional complex with mTOR/raptor to transduce mitogenic signals. *Cell. Signal.* 18 (2006) 2283-2291, which is hereby incorporated by reference). Again, these relations suggest that PLD2 is a new binding protein that has physical and functional connections with the mTOR complex.

Figure 16:
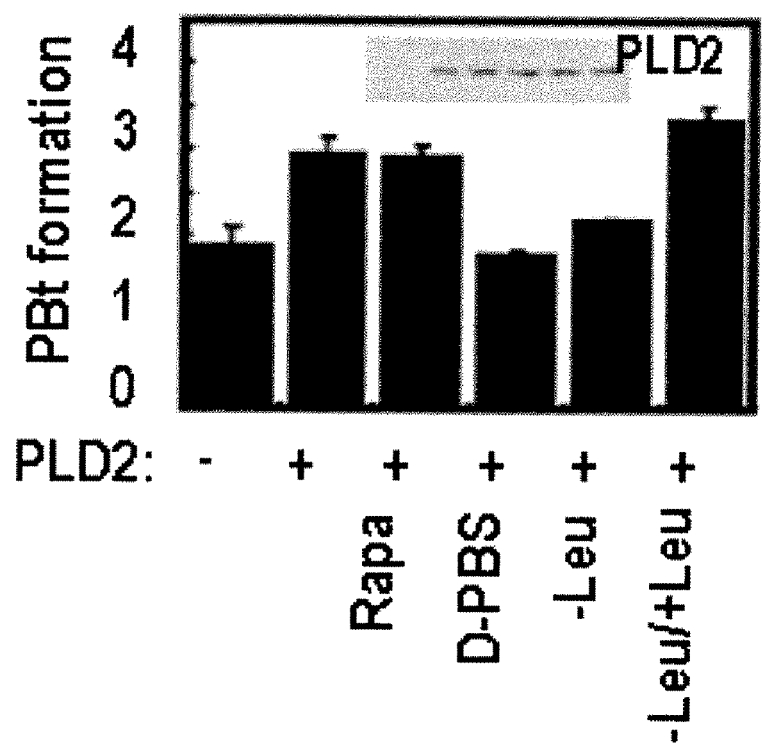
FIG. 16 shows the level of PBt formation in presence or absence of leucine.

Until now, the function of PLD2 in nutrient signaling has not been proposed. To this end, the importance of PLD2 in nutrient signaling was tested. The stimulatory effect of leucine on S6K1 was significantly reduced by 1-butanol. Based on the result, PLD2 activity in response to nutrient levels was checked. PLD2$^{wt}$ was transfected and allowed to express for 24 hr. After serum-deprivation for 16 hr and labeling with [$^3$H]myristic acid (2(Ci/ml) for 8 hr, cells were treated with rapamycin (20 nM), D-PBS, and leucine-free media (biowhittaker). After 45 min, same treatments including leucine-added media were added with 0.4% 1-butanol to measure PBt formation. The obtained results were shown in FIG. 16, indicating that PLD2 activity was reversibly regulated by amino acid levels, especially by leucine levels.

Figure 17:
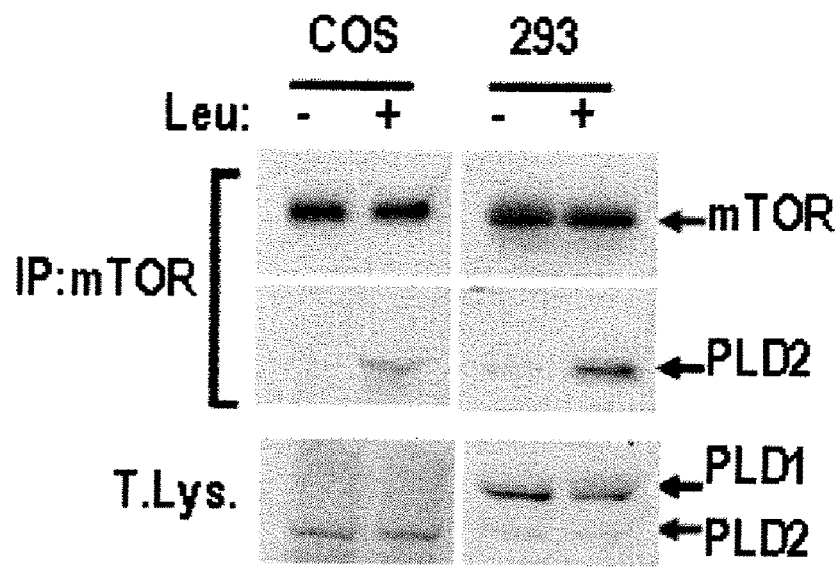
FIG. 17 shows IP analysis results using anti-mTOR antibody in COS7 and HEK293 cells in presence or absence of leucine.

To reveal the relationship between PLD2 activity and complex formation, the interaction between PLD2 and mTOR was tested. mTOR inhibition by rapamycin, which is a mTOR specific inhibitor, had no effect on the interaction between PLD2 and mTOR. However, the interaction between endogenous PLD2 and endogenous mTOR complex was increased by leucine treatment in leucine-deprived COS7 and HEK293 cells as shown FIG. 17. The results in FIG. 17 were obtained by lysing confluent COS7 and HEK293 cells and immunoprecipitating with anti-mTOR antibody after treating leucine-deprived cells with leucine.

Figure 18:
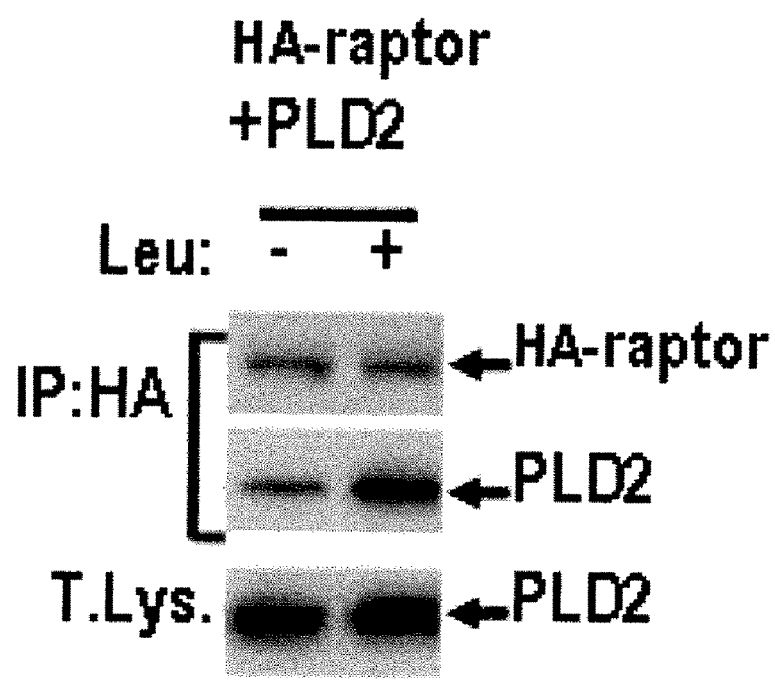
FIG. 18 shows the western blot analysis results in HA-raptor$^{wt}$/PLD2$^{wt}$ transfectant after leucine treatment.

Either HA-raptor$^{wt}$/PLD2$^{wt}$ or HA-Rheb/PLD2$^{wt}$ was transfected into HEK293 cells, and the cells were subjected to leucine deprivation. Co-IP after leucine treatment was followed by Western blot analysis. The results were shown in FIGS. 18 (for HA-raptor$^{wt}$/PLD2$^{wt}$) and 19 (HA-Rheb$^{wt}$/PLD2$^{wt}$). The increase by leucine was attributed to enhanced binding between PLD2 and raptor, as shown in FIG. 18. Importantly, the interaction between Rheb and PLD2 was also regulated by nutrient levels such that this interaction was stabilized under high nutrient conditions and weakened under low nutrient conditions, which allowed a nutrient-dependent mTOR complex composed of mTOR, raptor, PLD2, and Rheb to be identified, as shown in FIG. 19. These results are well correlated with reversible regulation of PLD2 activity against the level of leucine.

Example 15

Essential Role of PLD2/Rheb Interaction in Nutrient (Leucine) Signaling

Figure 20:
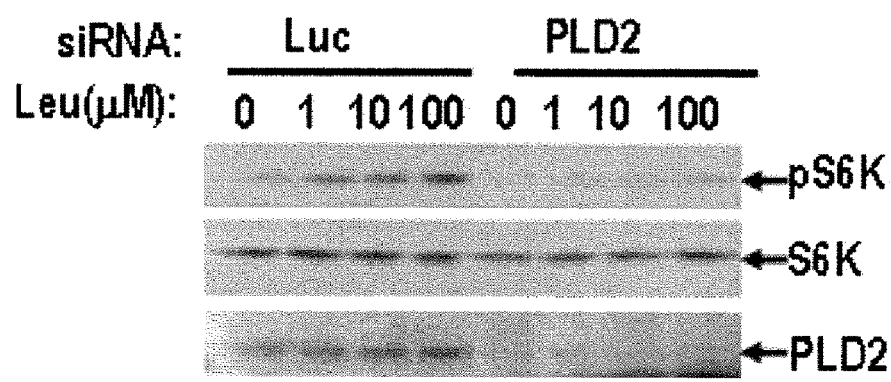
FIG. 20 shows the western blot analysis results in PLD2 siRNA transfectant after leucine treatment.

After transfecting PLD2 siRNA, cells were deprived of leucine for 45 min. The cells were treated with various concentration of leucine (0-100 μM) for 15 min and the resulting lysates were used for Western blot analysis. The obtained results were shown in FIG. 20. As shown in FIG. 20, it was found that PLD2 silencing completely downregulated the effect of leucine on S6K1 phosphorylation.

Figure 21:
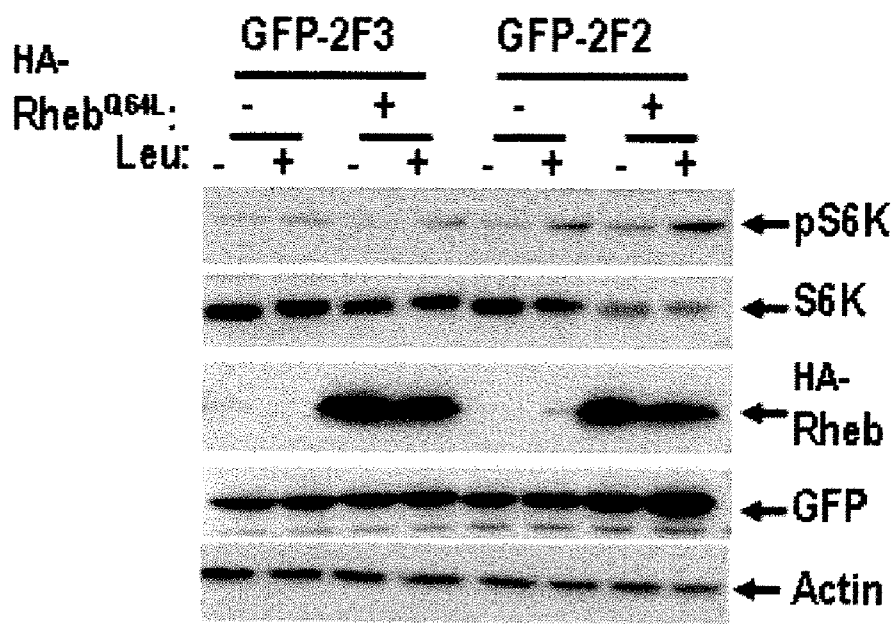
FIG. 21 shows the western blot analysis results in HA-Rheb$^{Q64L}$ transfected with either GFP-2F3 or GFP-2F2.

Further, HA-Rheb$^{Q64L}$ was transfected with either GFP-2F3 or GFP-2F2 and the resulting cells were subjected to leucine deprivation for 45 min. After leucine (100 μM) treatment for 15 min, the cell lysates were used for Western blot analysis. The obtained results were shown in FIG. 21, showing that the effect of leucine on S6K1 phosphorylation was specifically downregulated when GFP-2F3 was overexpressed. Such results suggest the importance of Rheb/PLD2 binding on leucine-induced mTOR signaling.

Figure 22:
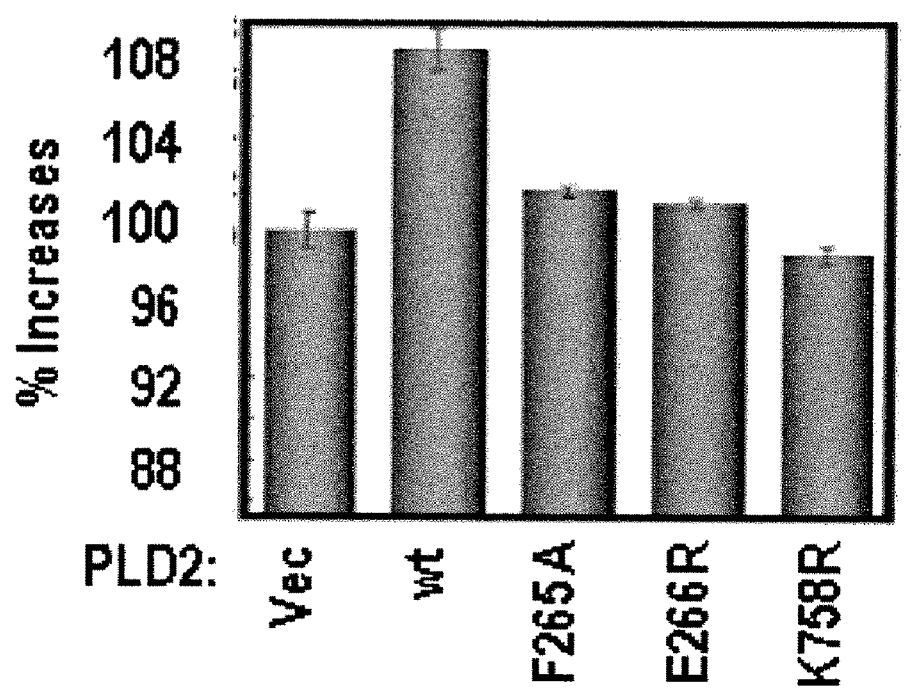
FIG. 22 shows the changes in cell size after transfecting various PLD2 mutants.

This increased mTOR activity was found to be well correlated with the regulation of cell growth, the control of cell size. After transfecting the PLD2 mutants as indicated in FIG. 22, cells were cultured to confluence. Cell sizes were determined after replating these cells for 48 hr, using a Multisizer 3 (Beckman Coulter), as described in "Kim, D. H., et al. mTOR interacts with raptor to form a nutrient-sensitive complex that signals to the cell growth machinery. *Cell* 110, 163-175 (2002)", which is hereby incorporated by reference. The obtained results were shown in FIG. 22, showing that PLD2 overexpression increased cell size in a TOS-motif dependent manner. Such results demonstrate the functional role of PLD2 in mTOR signaling for cell growth control, which is achieved via mTOR/raptor/PLD2/Rheb complex formation.

What is claimed is:

1. A method of inhibiting the interaction between phospholipase D2 (PLD2) and Ras homolog enriched in brain (Rheb) comprising the step of deleting or substituting one or more amino acids from the amino acid residues from position 476 to position 612 of SEQ ID NO:3, resulting in inhibiting interaction between PLD2 and Rheb.

2. A method of treating mTOR-related metabolic disease selected from the group consisting of cancer, diabetes, obesity, hamartoma syndromes and tissue/organ hypertrophy, comprising administering to a patient in need thereof an effective amount of a protein having a deletion or a substitution of one or more amino acids from the amino acid residues from position 476 to position 612 of SEQ ID NO:3 resulting in inhibiting the interaction between PLD2 and Rheb.

3. A modified PLD2 protein or fragment thereof comprising a Rheb binding site of PLD2 having a deletion from position 476 to position 612 of SEQ ID NO:3.

* * * * *

SEQUENCE LISTING

<160> NUMBER OF SEQ ID NOS: 12

<210> SEQ ID NO 1
<211> LENGTH: 2549
<212> TYPE: PRT
<213> ORGANISM: Artificial Sequence
<220> FEATURE:
<223> OTHER INFORMATION: Amino acid sequence of mammalian target-of-
      rapamycin (mTOR) [Homo sapiens]

<400> SEQUENCE: 1

```
Met Leu Gly Thr Gly Pro Ala Ala Thr Thr Ala Ala Thr Thr Ser
1               5                   10                  15

Ser Asn Val Ser Val Leu Gln Gln Phe Ala Ser Gly Leu Lys Ser Arg
                20                  25                  30

Asn Glu Glu Thr Arg Ala Lys Ala Ala Lys Glu Leu Gln His Tyr Val
            35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350
```

```
Lys Ser Thr Leu Val Glu Ser Arg Cys Cys Arg Asp Leu Met Glu Glu
            355                 360                 365
Lys Phe Asp Gln Val Cys Gln Trp Val Leu Lys Cys Arg Asn Ser Lys
            370                 375                 380
Asn Ser Leu Ile Gln Met Thr Ile Leu Asn Leu Pro Arg Leu Ala
385                 390                 395                 400
Ala Phe Arg Pro Ser Ala Phe Thr Asp Thr Gln Tyr Leu Gln Asp Thr
            405                 410                 415
Met Asn His Val Leu Ser Cys Val Lys Lys Glu Lys Glu Arg Thr Ala
            420                 425                 430
Ala Phe Gln Ala Leu Gly Leu Leu Ser Val Ala Val Arg Ser Glu Phe
            435                 440                 445
Lys Val Tyr Leu Pro Arg Val Leu Asp Ile Ile Arg Ala Ala Leu Pro
            450                 455                 460
Pro Lys Asp Phe Ala His Lys Arg Gln Lys Ala Met Gln Val Asp Ala
465                 470                 475                 480
Thr Val Phe Thr Cys Ile Ser Met Leu Ala Arg Ala Met Gly Pro Gly
            485                 490                 495
Ile Gln Gln Asp Ile Lys Glu Leu Leu Glu Pro Met Leu Ala Val Gly
            500                 505                 510
Leu Ser Pro Ala Leu Thr Ala Val Leu Tyr Asp Leu Ser Arg Gln Ile
            515                 520                 525
Pro Gln Leu Lys Lys Asp Ile Gln Asp Gly Leu Leu Lys Met Leu Ser
            530                 535                 540
Leu Val Leu Met His Lys Pro Leu Arg His Pro Gly Met Pro Lys Gly
545                 550                 555                 560
Leu Ala His Gln Leu Ala Ser Pro Gly Leu Thr Thr Leu Pro Glu Ala
            565                 570                 575
Ser Asp Val Gly Ser Ile Thr Leu Ala Leu Arg Thr Leu Gly Ser Phe
            580                 585                 590
Glu Phe Glu Gly His Ser Leu Thr Gln Phe Val Arg His Cys Ala Asp
            595                 600                 605
His Phe Leu Asn Ser Glu His Lys Glu Ile Arg Met Glu Ala Ala Arg
            610                 615                 620
Thr Cys Ser Arg Leu Leu Thr Pro Ser Ile His Leu Ile Ser Gly His
625                 630                 635                 640
Ala His Val Val Ser Gln Thr Ala Val Gln Val Ala Asp Val Leu
            645                 650                 655
Ser Lys Leu Leu Val Val Gly Ile Thr Asp Pro Asp Pro Asp Ile Arg
            660                 665                 670
Tyr Cys Val Leu Ala Ser Leu Asp Glu Arg Phe Asp Ala His Leu Ala
            675                 680                 685
Gln Ala Glu Asn Leu Gln Ala Leu Phe Val Ala Leu Asn Asp Gln Val
            690                 695                 700
Phe Glu Ile Arg Glu Leu Ala Ile Cys Thr Val Gly Arg Leu Ser Ser
705                 710                 715                 720
Met Asn Pro Ala Phe Val Met Pro Phe Leu Arg Lys Met Leu Ile Gln
            725                 730                 735
Ile Leu Thr Glu Leu Glu His Ser Gly Ile Gly Arg Ile Lys Glu Gln
            740                 745                 750
Ser Ala Arg Met Leu Gly His Leu Val Ser Asn Ala Pro Arg Leu Ile
            755                 760                 765
Arg Pro Tyr Met Glu Pro Ile Leu Lys Ala Leu Ile Leu Lys Leu Lys
```

```
              770               775                780
Asp Pro Asp Pro Asp Pro Asn Pro Gly Val Ile Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Met Asp Met Leu Gln Asp Ser Ser
                820                 825                 830

Leu Leu Ala Lys Arg Gln Val Ala Leu Trp Thr Leu Gly Gln Leu Val
                835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880

Arg Arg Glu Ala Ile Arg Val Gly Leu Leu Gly Ala Leu Asp Pro
                885                 890                 895

Tyr Lys His Lys Val Asn Ile Gly Met Ile Asp Gln Ser Arg Asp Ala
                900                 905                 910

Ser Ala Val Ser Leu Ser Glu Ser Lys Ser Ser Gln Asp Ser Ser Asp
                915                 920                 925

Tyr Ser Thr Ser Glu Met Leu Val Asn Met Gly Asn Leu Pro Leu Asp
930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
                995                 1000                1005

Arg Glu Phe Leu Phe Gln Gln Leu Gly Met Leu Val Ser Phe Val
                1010                1015                1020

Lys Ser His Ile Arg Pro Tyr Met Asp Glu Ile Val Thr Leu Met
                1025                1030                1035

Arg Glu Phe Trp Val Met Asn Thr Ser Ile Gln Ser Thr Ile Ile
                1040                1045                1050

Leu Leu Ile Glu Gln Ile Val Val Ala Leu Gly Gly Glu Phe Lys
                1055                1060                1065

Leu Tyr Leu Pro Gln Leu Ile Pro His Met Leu Arg Val Phe Met
                1070                1075                1080

His Asp Asn Ser Pro Gly Arg Ile Val Ser Ile Lys Leu Leu Ala
                1085                1090                1095

Ala Ile Gln Leu Phe Gly Ala Asn Leu Asp Asp Tyr Leu His Leu
                1100                1105                1110

Leu Leu Pro Pro Ile Val Lys Leu Phe Asp Ala Pro Glu Ala Pro
                1115                1120                1125

Leu Pro Ser Arg Lys Ala Ala Leu Glu Thr Val Asp Arg Leu Thr
                1130                1135                1140

Glu Ser Leu Asp Phe Thr Asp Tyr Ala Ser Arg Ile Ile His Pro
                1145                1150                1155

Ile Val Arg Thr Leu Asp Gln Ser Pro Glu Leu Arg Ser Thr Ala
                1160                1165                1170

Met Asp Thr Leu Ser Ser Leu Val Phe Gln Leu Gly Lys Lys Tyr
                1175                1180                1185
```

-continued

```
Gln Ile Phe Ile Pro Met Val Asn Lys Val Leu Val Arg His Arg
            1190            1195                1200

Ile Asn His Gln Arg Tyr Asp Val Leu Ile Cys Arg Ile Val Lys
1205                1210                1215

Gly Tyr Thr Leu Ala Asp Glu Glu Asp Pro Leu Ile Tyr Gln
    1220                1225                1230

His Arg Met Leu Arg Ser Gly Gln Gly Asp Ala Leu Ala Ser Gly
1235                1240                1245

Pro Val Glu Thr Gly Pro Met Lys Lys Leu His Val Ser Thr Ile
    1250                1255                1260

Asn Leu Gln Lys Ala Trp Gly Ala Ala Arg Arg Val Ser Lys Asp
1265                1270                1275

Asp Trp Leu Glu Trp Leu Arg Arg Leu Ser Leu Glu Leu Leu Lys
    1280                1285                1290

Asp Ser Ser Ser Pro Ser Leu Arg Ser Cys Trp Ala Leu Ala Gln
1295                1300                1305

Ala Tyr Asn Pro Met Ala Arg Asp Leu Phe Asn Ala Ala Phe Val
    1310                1315                1320

Ser Cys Trp Ser Glu Leu Asn Glu Asp Gln Gln Asp Glu Leu Ile
1325                1330                1335

Arg Ser Ile Glu Leu Ala Leu Thr Ser Gln Asp Ile Ala Glu Val
    1340                1345                1350

Thr Gln Thr Leu Leu Asn Leu Ala Glu Phe Met Glu His Ser Asp
1355                1360                1365

Lys Gly Pro Leu Pro Leu Arg Asp Asp Asn Gly Ile Val Leu Leu
    1370                1375                1380

Gly Glu Arg Ala Ala Lys Cys Arg Ala Tyr Ala Lys Ala Leu His
1385                1390                1395

Tyr Lys Glu Leu Glu Phe Gln Lys Gly Pro Thr Pro Ala Ile Leu
    1400                1405                1410

Glu Ser Leu Ile Ser Ile Asn Asn Lys Leu Gln Gln Pro Glu Ala
1415                1420                1425

Ala Ala Gly Val Leu Glu Tyr Ala Met Lys His Phe Gly Glu Leu
    1430                1435                1440

Glu Ile Gln Ala Thr Trp Tyr Glu Lys Leu His Glu Trp Glu Asp
1445                1450                1455

Ala Leu Val Ala Tyr Asp Lys Lys Met Asp Thr Asn Lys Asp Asp
    1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
    1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
    1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
    1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
    1580                1585                1590
```

```
His Met Leu Ser Glu Leu Glu Glu Val Ile Gln Tyr Lys Leu Val
    1595            1600                1605

Pro Glu Arg Arg Glu Ile Ile Arg Gln Ile Trp Trp Glu Arg Leu
    1610            1615                1620

Gln Gly Cys Gln Arg Ile Val Glu Asp Trp Gln Lys Ile Leu Met
    1625            1630                1635

Val Arg Ser Leu Val Val Ser Pro His Glu Asp Met Arg Thr Trp
    1640            1645                1650

Leu Lys Tyr Ala Ser Leu Cys Gly Lys Ser Gly Arg Leu Ala Leu
    1655            1660                1665

Ala His Lys Thr Leu Val Leu Leu Leu Gly Val Asp Pro Ser Arg
    1670            1675                1680

Gln Leu Asp His Pro Leu Pro Thr Val His Pro Gln Val Thr Tyr
    1685            1690                1695

Ala Tyr Met Lys Asn Met Trp Lys Ser Ala Arg Lys Ile Asp Ala
    1700            1705                1710

Phe Gln His Met Gln His Phe Val Gln Thr Met Gln Gln Gln Ala
    1715            1720                1725

Gln His Ala Ile Ala Thr Glu Asp Gln Gln His Lys Gln Glu Leu
    1730            1735                1740

His Lys Leu Met Ala Arg Cys Phe Leu Lys Leu Gly Glu Trp Gln
    1745            1750                1755

Leu Asn Leu Gln Gly Ile Asn Glu Ser Thr Ile Pro Lys Val Leu
    1760            1765                1770

Gln Tyr Tyr Ser Ala Ala Thr Glu His Asp Arg Ser Trp Tyr Lys
    1775            1780                1785

Ala Trp His Ala Trp Ala Val Met Asn Phe Glu Ala Val Leu His
    1790            1795                1800

Tyr Lys His Gln Asn Gln Ala Arg Asp Glu Lys Lys Lys Leu Arg
    1805            1810                1815

His Ala Ser Gly Ala Asn Ile Thr Asn Ala Thr Thr Ala Ala Thr
    1820            1825                1830

Thr Ala Ala Thr Ala Thr Thr Thr Ala Ser Thr Glu Gly Ser Asn
    1835            1840                1845

Ser Glu Ser Glu Ala Glu Ser Thr Glu Asn Ser Pro Thr Pro Ser
    1850            1855                1860

Pro Leu Gln Lys Lys Val Thr Glu Asp Leu Ser Lys Thr Leu Leu
    1865            1870                1875

Met Tyr Thr Val Pro Ala Val Gln Gly Phe Phe Arg Ser Ile Ser
    1880            1885                1890

Leu Ser Arg Gly Asn Asn Leu Gln Asp Thr Leu Arg Val Leu Thr
    1895            1900                1905

Leu Trp Phe Asp Tyr Gly His Trp Pro Asp Val Asn Glu Ala Leu
    1910            1915                1920

Val Glu Gly Val Lys Ala Ile Gln Ile Asp Thr Trp Leu Gln Val
    1925            1930                1935

Ile Pro Gln Leu Ile Ala Arg Ile Asp Thr Pro Arg Pro Leu Val
    1940            1945                1950

Gly Arg Leu Ile His Gln Leu Leu Thr Asp Ile Gly Arg Tyr His
    1955            1960                1965

Pro Gln Ala Leu Ile Tyr Pro Leu Thr Val Ala Ser Lys Ser Thr
    1970            1975                1980

Thr Thr Ala Arg His Asn Ala Ala Asn Lys Ile Leu Lys Asn Met
```

```
          1985                1990                1995
Cys Glu His Ser Asn Thr Leu Val Gln Gln Ala Met Met Val Ser
    2000                2005                2010
Glu Glu Leu Ile Arg Val Ala Ile Leu Trp His Glu Met Trp His
    2015                2020                2025
Glu Gly Leu Glu Glu Ala Ser Arg Leu Tyr Phe Gly Glu Arg Asn
    2030                2035                2040
Val Lys Gly Met Phe Glu Val Leu Glu Pro Leu His Ala Met Met
    2045                2050                2055
Glu Arg Gly Pro Gln Thr Leu Lys Glu Thr Ser Phe Asn Gln Ala
    2060                2065                2070
Tyr Gly Arg Asp Leu Met Glu Ala Gln Glu Trp Cys Arg Lys Tyr
    2075                2080                2085
Met Lys Ser Gly Asn Val Lys Asp Leu Thr Gln Ala Trp Asp Leu
    2090                2095                2100
Tyr Tyr His Val Phe Arg Arg Ile Ser Lys Gln Leu Pro Gln Leu
    2105                2110                2115
Thr Ser Leu Glu Leu Gln Tyr Val Ser Pro Lys Leu Leu Met Cys
    2120                2125                2130
Arg Asp Leu Glu Leu Ala Val Pro Gly Thr Tyr Asp Pro Asn Gln
    2135                2140                2145
Pro Ile Ile Arg Ile Gln Ser Ile Ala Pro Ser Leu Gln Val Ile
    2150                2155                2160
Thr Ser Lys Gln Arg Pro Arg Lys Leu Thr Leu Met Gly Ser Asn
    2165                2170                2175
Gly His Glu Phe Val Phe Leu Leu Lys Gly His Glu Asp Leu Arg
    2180                2185                2190
Gln Asp Glu Arg Val Met Gln Leu Phe Gly Leu Val Asn Thr Leu
    2195                2200                2205
Leu Ala Asn Asp Pro Thr Ser Leu Arg Lys Asn Leu Ser Ile Gln
    2210                2215                2220
Arg Tyr Ala Val Ile Pro Leu Ser Thr Asn Ser Gly Leu Ile Gly
    2225                2230                2235
Trp Val Pro His Cys Asp Thr Leu His Ala Leu Ile Arg Asp Tyr
    2240                2245                2250
Arg Glu Lys Lys Lys Ile Leu Leu Asn Ile Glu His Arg Ile Met
    2255                2260                2265
Leu Arg Met Ala Pro Asp Tyr Asp His Leu Thr Leu Met Gln Lys
    2270                2275                2280
Val Glu Val Phe Glu His Ala Val Asn Asn Thr Ala Gly Asp Asp
    2285                2290                2295
Leu Ala Lys Leu Leu Trp Leu Lys Ser Pro Ser Ser Glu Val Trp
    2300                2305                2310
Phe Asp Arg Arg Thr Asn Tyr Thr Arg Ser Leu Ala Val Met Ser
    2315                2320                2325
Met Val Gly Tyr Ile Leu Gly Leu Gly Asp Arg His Pro Ser Asn
    2330                2335                2340
Leu Met Leu Asp Arg Leu Ser Gly Lys Ile Leu His Ile Asp Phe
    2345                2350                2355
Gly Asp Cys Phe Glu Val Ala Met Thr Arg Glu Lys Phe Pro Glu
    2360                2365                2370
Lys Ile Pro Phe Arg Leu Thr Arg Met Leu Thr Asn Ala Met Glu
    2375                2380                2385
```

-continued

```
Val Thr Gly Leu Asp Gly Asn Tyr Arg Ile Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 2
<211> LENGTH: 1036
<212> TYPE: PRT
<213> ORGANISM: Artificial Sequence
<220> FEATURE:
<223> OTHER INFORMATION: Amino acid sequence of phospholipase D1 [Rattus
      norvegicus]
<220> FEATURE:
<221> NAME/KEY: misc_feature
<222> LOCATION: (719)..(719)
<223> OTHER INFORMATION: Xaa can be any naturally occurring amino acid

<400> SEQUENCE: 2

Met Ser Leu Arg Ser Glu Ala Arg Val Asn Thr Ser Thr Leu Gln Lys
1               5                   10                  15

Ile Ala Ala Asp Met Arg Asn Leu Ile Glu Asn Leu Asp Thr Arg Glu
            20                  25                  30

Leu His Phe Glu Gly Glu Glu Val Glu Tyr Asp Ala Ser Pro Gly Asp
        35                  40                  45

Pro Thr Ala Gln Glu Ala Cys Ile Pro Phe Ser Ser Ile Tyr Asn Thr
    50                  55                  60

Gln Gly Phe Lys Glu Pro Asn Ile Gln Ile Tyr Leu Ser Gly Cys Pro
65                  70                  75                  80

Val Lys Ala Gln Val Leu Glu Val Glu Arg Phe Thr Ser Thr Ser Arg
                85                  90                  95

Met Pro Ser Val Asn Leu Tyr Thr Ile Glu Leu Thr His Gly Glu Phe
            100                 105                 110

Thr Trp Gln Val Lys Arg Lys Phe Lys His Phe Gln Glu Phe His Arg
        115                 120                 125

Glu Leu Leu Lys Tyr Lys Ala Phe Ile Arg Ile Pro Ile Pro Thr Lys
    130                 135                 140

Arg His Thr Phe Arg Arg Gln Asn Val Lys Glu Glu Pro Arg Glu Met
145                 150                 155                 160

Pro Ser Leu Pro Arg Ser Ser Glu Asn Ala Ile Gln Glu Glu Gln Phe
                165                 170                 175
```

```
Phe Gly Arg Arg Lys Gln Leu Glu Asp Tyr Leu Thr Lys Ile Leu Lys
            180                 185                 190

Met Pro Met Tyr Arg Asn Tyr His Ala Thr Thr Glu Phe Leu Asp Val
            195                 200                 205

Ser Gln Leu Ser Phe Ile His Asp Leu Gly Pro Lys Gly Leu Glu Gly
        210                 215                 220

Met Ile Met Lys Arg Ser Gly Gly His Arg Ile Pro Gly Val Asn Cys
225                 230                 235                 240

Cys Gly His Gly Arg Ala Cys Tyr Arg Trp Ser Lys Arg Trp Leu Ile
                245                 250                 255

Val Lys Asp Ser Phe Leu Leu Tyr Met Lys Pro Asp Ser Gly Ala Ile
                260                 265                 270

Ala Phe Val Leu Leu Val Asp Lys Glu Phe Arg Ile Lys Val Gly Lys
            275                 280                 285

Lys Glu Thr Glu Thr Lys Tyr Gly Leu Arg Ile Asp Asn Leu Ser Arg
        290                 295                 300

Thr Leu Ile Leu Lys Cys Asn Ser Tyr Arg His Ala Arg Trp Trp Gly
305                 310                 315                 320

Gly Ala Ile Glu Glu Phe Ile Gln Lys His Gly Thr Asp Phe Leu Lys
                325                 330                 335

Asp His Arg Phe Gly Ser Tyr Ala Ala Val His Glu Asn Ile Leu Ala
                340                 345                 350

Lys Trp Tyr Val Asn Ala Lys Gly Tyr Phe Glu Asp Ile Ala Asn Ala
            355                 360                 365

Met Glu Gly Ala Thr Glu Glu Ile Phe Ile Thr Asp Trp Trp Leu Ser
            370                 375                 380

Pro Glu Ile Phe Leu Lys Arg Pro Val Val Glu Gly Asn Arg Trp Arg
385                 390                 395                 400

Leu Asp Cys Ile Leu Lys Arg Lys Ala Gln Gln Gly Val Arg Ile Phe
                405                 410                 415

Ile Met Leu Tyr Lys Glu Val Glu Leu Ala Leu Gly Ile Asn Ser Glu
            420                 425                 430

Tyr Thr Lys Arg Thr Leu Met Arg Leu His Pro Asn Ile Lys Val Met
            435                 440                 445

Arg His Pro Asp His Val Ser Ser Ser Val Tyr Leu Trp Ala His His
450                 455                 460

Glu Lys Leu Val Ile Ile Asp Gln Ser Val Ala Phe Val Gly Gly Ile
465                 470                 475                 480

Asp Leu Ala Tyr Gly Arg Trp Asp Asp Asn Glu His Arg Leu Thr Asp
                485                 490                 495

Val Gly Ser Val Lys Arg Val Thr Ser Gly Gln Ser Leu Gly Ser Leu
            500                 505                 510

Thr Ala Ala Ser Val Glu Ser Met Glu Ser Leu Ser Leu Lys Asp Lys
            515                 520                 525

His Gln Ser His Lys Asn Glu Pro Val Leu Lys Ser Val Asn Asp Thr
        530                 535                 540

Asp Met Lys Leu Lys Gly Ile Gly Lys Ser Arg Lys Phe Ser Lys Phe
545                 550                 555                 560

Ser Leu Tyr Arg Gln Leu His Arg Arg Asn Leu His Asn Ser Asp Ser
                565                 570                 575

Ile Ser Ser Val Asp Ser Ala Ser Asn Thr Gly Ser Ile Arg Ser Val
            580                 585                 590

Gln Thr Gly Val Gly Glu Leu His Gly Glu Thr Arg Phe Trp His Gly
```

```
                595                 600                 605
Lys Asp Tyr Cys Asn Phe Val Phe Lys Asp Trp Val Gln Leu Asp Lys
610                 615                 620

Pro Phe Ala Asp Phe Ile Asp Arg Tyr Ser Thr Pro Arg Met Pro Trp
625                 630                 635                 640

His Asp Ile Gly Ser Val Val His Gly Lys Ala Ala Arg Asp Val Ala
                645                 650                 655

Arg His Phe Ile Gln Arg Trp Asn Phe Thr Lys Ile Met Lys Pro Lys
                660                 665                 670

Tyr Arg Ser Leu Ser Tyr Pro Phe Leu Leu Pro Lys Ser Gln Ala Thr
                675                 680                 685

Ala His Glu Leu Arg Tyr Gln Val Pro Gly Ala Val His Ala Lys Ala
690                 695                 700

Gln Leu Leu Arg Ser Ala Ala Asp Trp Ser Ala Gly Ile Lys Xaa His
705                 710                 715                 720

Glu Glu Ser Ile His Ala Ala Tyr Thr His Val Ile Glu Asn Ser Lys
                725                 730                 735

His Tyr Ile Tyr Ile Glu Asn Gln Phe Phe Ile Ser Cys Ala Asp Asp
                740                 745                 750

Lys Val Val Phe Asn Lys Val Gly Asn Ala Ile Ala Gln Arg Ile Leu
                755                 760                 765

Lys Ala His Arg Glu Gly Gln Arg Tyr Arg Val Tyr Ile Val Ile Pro
770                 775                 780

Leu Leu Pro Gly Phe Glu Gly Asp Ile Ser Thr Gly Gly Gly Asn Ala
785                 790                 795                 800

Leu Gln Ala Ile Met His Phe Asn Tyr Arg Thr Met Cys Arg Gly Glu
                805                 810                 815

Ser Ser Ile Leu Glu Gln Leu Lys Pro Glu Leu Gly Asn Lys Trp Ile
                820                 825                 830

Asn Tyr Ile Ser Phe Cys Gly Leu Arg Thr His Ala Glu Leu Glu Gly
                835                 840                 845

Asn Leu Val Thr Glu Leu Ile Tyr Val His Ser Lys Leu Leu Ile Ala
                850                 855                 860

Asp Asp Asn Thr Val Ile Ile Gly Ser Ala Asn Ile Asn Asp Arg Ser
865                 870                 875                 880

Met Leu Gly Lys Arg Asp Ser Glu Met Ala Val Ile Val Gln Asp Arg
                885                 890                 895

Gln Thr Val Pro Ser Val Met Asp Gly Lys Glu Tyr Gln Ala Gly Arg
                900                 905                 910

Phe Ala Gln Gly Leu Arg Leu Glu Cys Phe Arg Leu Val Leu Gly Tyr
                915                 920                 925

Leu Ser Asp Pro Ser Glu Asp Ile Gln Asp Pro Val Ser Asp Lys Phe
930                 935                 940

Phe Lys Glu Ile Trp Val Ser Thr Ala Ala Arg Asn Ala Thr Ile Tyr
945                 950                 955                 960

Asp Lys Val Phe Arg Cys Leu Pro Asn Asp Glu Val His Asn Leu Ile
                965                 970                 975

Gln Leu Arg Asp Phe Ile Asn Lys Pro Ile Leu Ala Lys Glu Asp Arg
                980                 985                 990

Leu Arg Ala Glu Glu Glu Leu Arg  Lys Ile Arg Gly Phe Leu Val Gln
                995                 1000                1005

Phe Pro  Phe Tyr Phe Leu Ser  Glu Glu Asn Leu Leu  Pro Ser Val
    1010                1015                1020
```

```
Gly Thr Lys Glu Ala Ile Val Pro Met Glu Val Trp Thr
            1025                1030                1035

<210> SEQ ID NO 3
<211> LENGTH: 933
<212> TYPE: PRT
<213> ORGANISM: Artificial Sequence
<220> FEATURE:
<223> OTHER INFORMATION: Amino acid sequence of phospholipase D2 [Homo
      sapiens]

<400> SEQUENCE: 3

Met Thr Ala Thr Pro Glu Ser Leu Phe Pro Thr Gly Asp Glu Leu Asp
1               5                   10                  15

Ser Ser Gln Leu Gln Met Glu Ser Asp Glu Val Asp Thr Leu Lys Glu
            20                  25                  30

Gly Glu Asp Pro Ala Asp Arg Met His Pro Phe Leu Ala Ile Tyr Glu
        35                  40                  45

Leu Gln Ser Leu Lys Val His Pro Leu Val Phe Ala Pro Gly Val Pro
    50                  55                  60

Val Thr Ala Gln Val Val Gly Thr Glu Arg Tyr Thr Ser Gly Ser Lys
65                  70                  75                  80

Val Gly Thr Cys Thr Leu Tyr Ser Val Arg Leu Thr His Gly Asp Phe
                85                  90                  95

Ser Trp Thr Thr Lys Lys Lys Tyr Arg His Phe Gln Glu Leu His Arg
            100                 105                 110

Asp Leu Leu Arg His Lys Val Leu Met Ser Leu Leu Pro Leu Ala Arg
        115                 120                 125

Phe Ala Val Ala Tyr Ser Pro Ala Arg Asp Ala Gly Asn Arg Glu Met
    130                 135                 140

Pro Ser Leu Pro Arg Ala Gly Pro Glu Gly Ser Thr Arg His Ala Ala
145                 150                 155                 160

Ser Lys Gln Lys Tyr Leu Glu Asn Tyr Leu Asn Cys Leu Leu Thr Met
                165                 170                 175

Ser Phe Tyr Arg Asn Tyr His Ala Met Thr Glu Phe Leu Glu Val Ser
            180                 185                 190

Gln Leu Ser Phe Ile Pro Asp Leu Gly Arg Lys Gly Leu Glu Gly Met
        195                 200                 205

Ile Arg Lys Arg Ser Gly Gly His Arg Val Pro Gly Leu Thr Cys Cys
    210                 215                 220

Gly Arg Asp Gln Val Cys Tyr Arg Trp Ser Lys Arg Trp Leu Val Val
225                 230                 235                 240

Lys Asp Ser Phe Leu Leu Tyr Met Cys Leu Glu Thr Gly Ala Ile Ser
                245                 250                 255

Phe Val Gln Leu Phe Asp Pro Gly Phe Glu Val Gln Val Gly Lys Arg
            260                 265                 270

Ser Thr Glu Ala Arg His Gly Val Arg Ile Asp Thr Ser His Arg Ser
        275                 280                 285

Leu Ile Leu Lys Cys Ser Ser Tyr Arg Gln Ala Arg Trp Trp Ala Gln
    290                 295                 300

Glu Ile Thr Glu Leu Ala Gln Gly Pro Gly Arg Asp Phe Leu Gln Leu
305                 310                 315                 320

His Arg His Asp Ser Tyr Ala Pro Pro Arg Pro Gly Thr Leu Ala Arg
                325                 330                 335

Trp Phe Val Asn Gly Ala Gly Tyr Phe Ala Ala Val Ala Asp Ala Ile
            340                 345                 350
```

-continued

```
Leu Arg Ala Gln Glu Glu Ile Phe Ile Thr Asp Trp Trp Leu Ser Pro
        355                 360                 365

Glu Val Tyr Leu Lys Arg Pro Ala His Ser Asp Asp Trp Arg Leu Asp
370                 375                 380

Ile Met Leu Lys Arg Lys Ala Glu Gly Val Arg Val Ser Ile Leu
385                 390                 395                 400

Leu Phe Lys Glu Val Glu Leu Ala Leu Gly Ile Asn Ser Gly Tyr Ser
                405                 410                 415

Lys Arg Ala Leu Met Leu Leu His Pro Asn Ile Lys Val Met Arg His
                420                 425                 430

Pro Asp Gln Val Thr Leu Trp Ala His Glu Lys Leu Leu Val Val
        435                 440                 445

Asp Gln Val Val Ala Phe Leu Gly Gly Leu Asp Leu Ala Tyr Gly Arg
450                 455                 460

Trp Asp Asp Leu His Tyr Arg Leu Thr Asp Leu Gly Asp Ser Ser Glu
465                 470                 475                 480

Ser Ala Ala Ser Gln Pro Pro Thr Pro Arg Pro Asp Ser Pro Ala Thr
                485                 490                 495

Pro Asp Leu Ser His Asn Gln Phe Phe Trp Leu Gly Lys Asp Tyr Ser
                500                 505                 510

Asn Leu Ile Thr Lys Asp Trp Val Gln Leu Asp Arg Pro Phe Glu Asp
                515                 520                 525

Phe Ile Asp Arg Glu Thr Thr Pro Arg Met Pro Trp Arg Asp Val Gly
530                 535                 540

Val Val Val His Gly Leu Pro Ala Arg Asp Leu Ala Arg His Phe Ile
545                 550                 555                 560

Gln Arg Trp Asn Phe Thr Lys Thr Thr Lys Ala Lys Tyr Lys Thr Pro
                565                 570                 575

Ile Tyr Pro Tyr Leu Leu Pro Lys Ser Thr Ser Thr Ala Asn Gln Leu
                580                 585                 590

Pro Phe Thr Leu Pro Gly Gly Gln Cys Thr Thr Val Gln Val Leu Arg
                595                 600                 605

Ser Val Asp Arg Trp Ser Ala Gly Thr Leu Glu Asn Ser Ile Leu Asn
610                 615                 620

Ala Tyr Leu His Thr Ile Arg Glu Ser Gln His Phe Leu Tyr Ile Glu
625                 630                 635                 640

Asn Gln Phe Phe Ile Ser Cys Ser Asp Gly Arg Thr Val Leu Asn Lys
                645                 650                 655

Val Gly Asp Glu Ile Val Asp Arg Ile Leu Lys Ala His Lys Gln Gly
                660                 665                 670

Trp Cys Tyr Arg Val Tyr Val Leu Leu Pro Leu Leu Pro Gly Phe Glu
                675                 680                 685

Gly Asp Ile Ser Thr Gly Gly Gly Asn Ser Ile Gln Ala Ile Leu His
        690                 695                 700

Phe Thr Tyr Arg Thr Leu Cys Arg Gly Glu Tyr Ser Ile Leu His Arg
705                 710                 715                 720

Leu Lys Ala Ala Met Gly Thr Ala Trp Arg Asp Tyr Ile Ser Ile Cys
                725                 730                 735

Gly Leu Arg Thr His Gly Glu Leu Gly Gly His Pro Val Ser Glu Leu
                740                 745                 750

Ile Tyr Ile His Ser Lys Val Leu Ile Ala Asp Asp Arg Thr Val Ile
        755                 760                 765

Ile Gly Ser Ala Asn Ile Asn Asp Arg Ser Leu Leu Gly Lys Arg Asp
770                 775                 780
```

Ser Glu Leu Ala Val Leu Ile Glu Asp Thr Glu Thr Glu Pro Ser Leu
785                 790                 795                 800

Met Asn Gly Ala Glu Tyr Gln Ala Gly Arg Phe Ala Leu Ser Leu Arg
            805                 810                 815

Lys His Cys Phe Gly Val Ile Leu Gly Ala Asn Thr Arg Pro Asp Leu
            820                 825                 830

Asp Leu Arg Asp Pro Ile Cys Asp Asp Phe Phe Gln Leu Trp Gln Asp
        835                 840                 845

Met Ala Glu Ser Asn Ala Asn Ile Tyr Glu Gln Ile Phe Arg Cys Leu
850                 855                 860

Pro Ser Asn Ala Thr Arg Ser Leu Arg Thr Leu Arg Glu Tyr Val Ala
865                 870                 875                 880

Val Glu Pro Leu Ala Thr Val Ser Pro Leu Ala Arg Ser Glu Leu
            885                 890                 895

Thr Gln Val Gln Gly His Leu Val His Phe Pro Leu Lys Phe Leu Glu
            900                 905                 910

Asp Glu Ser Leu Leu Pro Pro Leu Gly Ser Lys Glu Gly Met Ile Pro
        915                 920                 925

Leu Glu Val Trp Thr
    930

<210> SEQ ID NO 4
<211> LENGTH: 184
<212> TYPE: PRT
<213> ORGANISM: Artificial Sequence
<220> FEATURE:
<223> OTHER INFORMATION: Amino acid sequence of Ras homolog enriched in
      brain [Homo sapiens]

<400> SEQUENCE: 4

Met Pro Gln Ser Lys Ser Arg Lys Ile Ala Ile Leu Gly Tyr Arg Ser
1               5                   10                  15

Val Gly Lys Ser Ser Leu Thr Ile Gln Phe Val Glu Gly Gln Phe Val
            20                  25                  30

Asp Ser Tyr Asp Pro Thr Ile Glu Asn Thr Phe Thr Lys Leu Ile Thr
        35                  40                  45

Val Asn Gly Gln Glu Tyr His Leu Gln Leu Val Asp Thr Ala Gly Gln
50                  55                  60

Asp Glu Tyr Ser Ile Phe Pro Gln Thr Tyr Ser Ile Asp Ile Asn Gly
65                  70                  75                  80

Tyr Ile Leu Val Tyr Ser Val Thr Ser Ile Lys Ser Phe Glu Val Ile
            85                  90                  95

Lys Val Ile His Gly Lys Leu Leu Asp Met Val Gly Lys Val Gln Ile
            100                 105                 110

Pro Ile Met Leu Val Gly Asn Lys Lys Asp Leu His Met Glu Arg Val
        115                 120                 125

Ile Ser Tyr Glu Glu Gly Lys Ala Leu Ala Glu Ser Trp Asn Ala Ala
130                 135                 140

Phe Leu Glu Ser Ser Ala Lys Glu Asn Gln Thr Ala Val Asp Val Phe
145                 150                 155                 160

Arg Arg Ile Ile Leu Glu Ala Glu Lys Met Asp Gly Ala Ala Ser Gln
            165                 170                 175

Gly Lys Ser Ser Cys Ser Val Met
            180

<210> SEQ ID NO 5

<211> LENGTH: 1335
<212> TYPE: PRT
<213> ORGANISM: Artificial Sequence
<220> FEATURE:
<223> OTHER INFORMATION: Amino acid sequence of regulatory-associated
       protein of mTOR (Raptor) (P150 target of rapamycin (TOR)-scaffold
       protein) [Homo sapiens]

<400> SEQUENCE: 5

```
Met Glu Ser Glu Met Leu Gln Ser Pro Leu Leu Gly Leu Gly Glu Glu
1               5                   10                  15

Asp Glu Ala Asp Leu Thr Asp Trp Asn Leu Pro Leu Ala Phe Met Lys
            20                  25                  30

Lys Arg His Cys Glu Lys Ile Glu Gly Ser Lys Ser Leu Ala Gln Ser
        35                  40                  45

Trp Arg Met Lys Asp Arg Met Lys Thr Val Ser Val Ala Leu Val Leu
    50                  55                  60

Cys Leu Asn Val Gly Val Asp Pro Pro Asp Val Val Lys Thr Thr Pro
65                  70                  75                  80

Cys Ala Arg Leu Glu Cys Trp Ile Asp Pro Leu Ser Met Gly Pro Gln
                85                  90                  95

Lys Ala Leu Glu Thr Ile Gly Ala Asn Leu Gln Lys Gln Tyr Glu Asn
            100                 105                 110

Trp Gln Pro Arg Ala Arg Tyr Lys Gln Ser Leu Asp Pro Thr Val Asp
        115                 120                 125

Glu Val Lys Lys Leu Cys Thr Ser Leu Arg Arg Asn Ala Lys Glu Glu
    130                 135                 140

Arg Val Leu Phe His Tyr Asn Gly His Gly Val Pro Arg Pro Thr Val
145                 150                 155                 160

Asn Gly Glu Val Trp Val Phe Asn Lys Asn Tyr Thr Gln Tyr Ile Pro
                165                 170                 175

Leu Ser Ile Tyr Asp Leu Gln Thr Trp Met Gly Ser Pro Ser Ile Phe
            180                 185                 190

Val Tyr Asp Cys Ser Asn Ala Gly Leu Ile Val Lys Ser Phe Lys Gln
        195                 200                 205

Phe Ala Leu Gln Arg Glu Gln Glu Leu Glu Val Ala Ala Ile Asn Pro
    210                 215                 220

Asn His Pro Leu Ala Gln Met Pro Leu Pro Pro Ser Met Lys Asn Cys
225                 230                 235                 240

Ile Gln Leu Ala Ala Cys Glu Ala Thr Glu Leu Leu Pro Met Ile Pro
                245                 250                 255

Asp Leu Pro Ala Asp Leu Phe Thr Ser Cys Leu Thr Thr Pro Ile Lys
            260                 265                 270

Ile Ala Leu Arg Trp Phe Cys Met Gln Lys Cys Val Ser Leu Val Pro
        275                 280                 285

Gly Val Thr Leu Asp Leu Ile Glu Lys Ile Pro Gly Arg Leu Asn Asp
    290                 295                 300

Arg Arg Thr Pro Leu Gly Glu Leu Asn Trp Ile Phe Thr Ala Ile Thr
305                 310                 315                 320

Asp Thr Ile Ala Trp Asn Val Leu Pro Arg Asp Leu Phe Gln Lys Leu
                325                 330                 335

Phe Arg Gln Asp Leu Leu Val Ala Ser Leu Phe Arg Asn Phe Leu Leu
            340                 345                 350

Ala Glu Arg Ile Met Arg Ser Tyr Asn Cys Thr Pro Val Ser Ser Pro
        355                 360                 365

Arg Leu Pro Pro Thr Tyr Met His Ala Met Trp Gln Ala Trp Asp Leu
```

```
            370                 375                 380
Ala Val Asp Ile Cys Leu Ser Gln Leu Pro Thr Ile Ile Glu Glu Gly
385                 390                 395                 400

Thr Ala Phe Arg His Ser Pro Phe Ala Glu Gln Leu Thr Ala Phe
            405                 410                 415

Gln Val Trp Leu Thr Met Gly Val Glu Asn Arg Asn Pro Pro Glu Gln
            420                 425                 430

Leu Pro Ile Val Leu Gln Val Leu Leu Ser Gln Val His Arg Leu Arg
            435                 440                 445

Ala Leu Asp Leu Leu Gly Arg Phe Leu Asp Leu Gly Pro Trp Ala Val
            450                 455                 460

Ser Leu Ala Leu Ser Val Gly Ile Phe Pro Tyr Val Leu Lys Leu Leu
465                 470                 475                 480

Gln Ser Ser Ala Arg Glu Leu Arg Pro Leu Leu Val Phe Ile Trp Ala
            485                 490                 495

Lys Ile Leu Ala Val Asp Ser Ser Cys Gln Ala Asp Leu Val Lys Asp
            500                 505                 510

Asn Gly His Lys Tyr Phe Leu Ser Val Leu Ala Asp Pro Tyr Met Pro
            515                 520                 525

Ala Glu His Arg Thr Met Thr Ala Phe Ile Leu Ala Val Ile Val Asn
            530                 535                 540

Ser Tyr His Thr Gly Gln Glu Ala Cys Leu Gln Gly Asn Leu Ile Ala
545                 550                 555                 560

Ile Cys Leu Glu Gln Leu Asn Asp Pro His Pro Leu Leu Arg Gln Trp
            565                 570                 575

Val Ala Ile Cys Leu Gly Arg Ile Trp Gln Asn Phe Asp Ser Ala Arg
            580                 585                 590

Trp Cys Gly Val Arg Asp Ser Ala His Glu Lys Leu Tyr Ser Leu Leu
            595                 600                 605

Ser Asp Pro Ile Pro Glu Val Arg Cys Ala Ala Val Phe Ala Leu Gly
            610                 615                 620

Thr Phe Val Gly Asn Ser Ala Glu Arg Thr Asp His Ser Thr Thr Ile
625                 630                 635                 640

Asp His Asn Val Ala Met Met Leu Ala Gln Leu Val Ser Asp Gly Ser
            645                 650                 655

Pro Met Val Arg Lys Glu Leu Val Val Ala Leu Ser His Leu Val Val
            660                 665                 670

Gln Tyr Glu Ser Asn Phe Cys Thr Val Ala Leu Gln Phe Ile Glu Glu
            675                 680                 685

Glu Lys Asn Tyr Ala Leu Pro Ser Pro Ala Thr Thr Glu Gly Gly Ser
            690                 695                 700

Leu Thr Pro Val Arg Asp Ser Pro Cys Thr Pro Arg Leu Arg Ser Val
705                 710                 715                 720

Ser Ser Tyr Gly Asn Ile Arg Ala Val Ala Thr Ala Arg Ser Leu Asn
            725                 730                 735

Lys Ser Leu Gln Asn Leu Ser Leu Thr Glu Glu Ser Gly Gly Ala Val
            740                 745                 750

Ala Phe Ser Pro Gly Asn Leu Ser Thr Ser Ser Ala Ser Ser Thr
            755                 760                 765

Leu Gly Ser Pro Glu Asn Glu Glu His Ile Leu Ser Phe Glu Thr Ile
            770                 775                 780

Asp Lys Met Arg Arg Ala Ser Ser Tyr Ser Ser Leu Asn Ser Leu Ile
785                 790                 795                 800
```

-continued

```
Gly Val Ser Phe Asn Ser Val Tyr Thr Gln Ile Trp Arg Val Leu Leu
                805                 810                 815

His Leu Ala Ala Asp Pro Tyr Pro Glu Val Ser Asp Val Ala Met Lys
            820                 825                 830

Val Leu Asn Ser Ile Ala Tyr Lys Ala Thr Val Asn Ala Arg Pro Gln
        835                 840                 845

Arg Val Leu Asp Thr Ser Ser Leu Thr Gln Ser Ala Pro Ala Ser Pro
    850                 855                 860

Thr Asn Lys Gly Val His Ile His Gln Ala Gly Gly Ser Pro Pro Ala
865                 870                 875                 880

Ser Ser Thr Ser Ser Ser Ser Leu Thr Asn Asp Val Ala Lys Gln Pro
                885                 890                 895

Val Ser Arg Asp Leu Pro Ser Gly Arg Pro Gly Thr Thr Gly Pro Ala
            900                 905                 910

Gly Ala Gln Tyr Thr Pro His Ser His Gln Phe Pro Arg Thr Arg Lys
        915                 920                 925

Met Phe Asp Lys Gly Pro Glu Gln Thr Ala Asp Ala Asp Asp Ala
    930                 935                 940

Ala Gly His Lys Ser Phe Ile Ser Ala Thr Val Gln Thr Gly Phe Cys
945                 950                 955                 960

Asp Trp Ser Ala Arg Tyr Phe Ala Gln Pro Val Met Lys Ile Pro Glu
                965                 970                 975

Glu His Asp Leu Glu Ser Gln Ile Arg Lys Glu Arg Glu Trp Arg Phe
            980                 985                 990

Leu Arg Asn Ser Arg Val Arg Arg Gln Ala Gln Gln Val Ile Gln Lys
        995                 1000                1005

Gly Ile Thr Arg Leu Asp Asp Gln Ile Phe Leu Asn Arg Asn Pro
    1010                1015                1020

Gly Val Pro Ser Val Val Lys Phe His Pro Phe Thr Pro Cys Ile
    1025                1030                1035

Ala Val Ala Asp Lys Asp Ser Ile Cys Phe Trp Asp Trp Glu Lys
    1040                1045                1050

Gly Glu Lys Leu Asp Tyr Phe His Asn Gly Asn Pro Arg Tyr Thr
    1055                1060                1065

Arg Val Thr Ala Met Glu Tyr Leu Asn Gly Gln Asp Cys Ser Leu
    1070                1075                1080

Leu Leu Thr Ala Thr Asp Asp Gly Ala Ile Arg Val Trp Lys Asn
    1085                1090                1095

Phe Ala Asp Leu Glu Lys Asn Pro Glu Met Val Thr Ala Trp Gln
    1100                1105                1110

Gly Leu Ser Asp Met Leu Pro Thr Thr Arg Gly Ala Gly Met Val
    1115                1120                1125

Val Asp Trp Glu Gln Glu Thr Gly Leu Leu Met Ser Ser Gly Asp
    1130                1135                1140

Val Arg Ile Val Arg Ile Trp Asp Thr Asp Arg Glu Met Lys Val
    1145                1150                1155

Gln Asp Ile Pro Thr Gly Ala Asp Ser Cys Val Thr Ser Leu Ser
    1160                1165                1170

Cys Asp Ser His Arg Ser Leu Ile Val Ala Gly Leu Gly Asp Gly
    1175                1180                1185

Ser Ile Arg Val Tyr Asp Arg Met Ala Leu Ser Glu Cys Arg
    1190                1195                1200

Val Met Thr Tyr Arg Glu His Thr Ala Trp Val Val Lys Ala Ser
    1205                1210                1215
```

```
Leu Gln Lys Arg Pro Asp Gly His Ile Val Ser Val Ser Val Asn
    1220                1225                1230

Gly Asp Val Arg Ile Phe Asp Pro Arg Met Pro Glu Ser Val Asn
        1235                1240                1245

Val Leu Gln Ile Val Lys Gly Leu Thr Ala Leu Asp Ile His Pro
    1250                1255                1260

Gln Ala Asp Leu Ile Ala Cys Gly Ser Val Asn Gln Phe Thr Ala
    1265                1270                1275

Ile Tyr Asn Ser Ser Gly Glu Leu Ile Asn Asn Ile Lys Tyr Tyr
    1280                1285                1290

Asp Gly Phe Met Gly Gln Arg Val Gly Ala Ile Ser Cys Leu Ala
    1295                1300                1305

Phe His Pro His Trp Pro His Leu Ala Val Gly Ser Asn Asp Tyr
    1310                1315                1320

Tyr Ile Ser Val Tyr Ser Val Glu Lys Arg Val Arg
    1325                1330                1335

<210> SEQ ID NO 6
<211> LENGTH: 24
<212> TYPE: DNA
<213> ORGANISM: Artificial Sequence
<220> FEATURE:
<223> OTHER INFORMATION: Sense oligonucleotide for PCR of PLD2

<400> SEQUENCE: 6
ggccgagacc aagtttgtta tcgc                                           24

<210> SEQ ID NO 7
<211> LENGTH: 65
<212> TYPE: DNA
<213> ORGANISM: Artificial Sequence
<220> FEATURE:
<223> OTHER INFORMATION: Antisense oligonucleotide (F265A)

<400> SEQUENCE: 7
ccatcgatcc gcacgccgtg ccgtgcctcc gtgctccttt tccccacttg cacctcagcg    60
ccagg                                                                65

<210> SEQ ID NO 8
<211> LENGTH: 65
<212> TYPE: DNA
<213> ORGANISM: Artificial Sequence
<220> FEATURE:
<223> OTHER INFORMATION: Antisense oligonucleotide (E266R)

<400> SEQUENCE: 8
ccatcgatcc gcacgccgtg ccgtgcctcc gtgctccttt tccccacttg caccctaaag    60
ccagg                                                                65

<210> SEQ ID NO 9
<211> LENGTH: 21
<212> TYPE: RNA
<213> ORGANISM: Artificial Sequence
<220> FEATURE:
<223> OTHER INFORMATION: Sense oligonucleotide corresponding to human
      PLD2 coding nucleotides 703-723

<400> SEQUENCE: 9
aagagguggc ugguggugaa g                                              21

<210> SEQ ID NO 10
```

-continued

```
<211> LENGTH: 21
<212> TYPE: RNA
<213> ORGANISM: Artificial Sequence
<220> FEATURE:
<223> OTHER INFORMATION: Antisense oligonucleotide corresponding to
      human PLD2 coding nucleotides 703-723

<400> SEQUENCE: 10
cuucaccacc agccaccucu u                                              21

<210> SEQ ID NO 11
<211> LENGTH: 21
<212> TYPE: DNA
<213> ORGANISM: Artificial Sequence
<220> FEATURE:
<223> OTHER INFORMATION: Fragment of human Rheb coding gene

<400> SEQUENCE: 11
gaggacactg ggaatatatt c                                              21

<210> SEQ ID NO 12
<211> LENGTH: 21
<212> TYPE: DNA
<213> ORGANISM: Artificial Sequence
<220> FEATURE:
<223> OTHER INFORMATION: Nucleotides 703-723 of PLD2

<400> SEQUENCE: 12
aagaggtggc tggtggtgaa g                                              21
```